US010024873B2

(12) United States Patent
Letourneau et al.

(10) Patent No.: US 10,024,873 B2
(45) Date of Patent: *Jul. 17, 2018

(54) METHODS AND APPARATUS FOR DETECTING COMPOUNDS IN LIQUIDS

(71) Applicant: Undercover Colors, Inc., Raleigh, NC (US)

(72) Inventors: Nicolas Letourneau, Raleigh, NC (US); Aly Khalifa, Raleigh, NC (US); Michael Gorczynski, Raleigh, NC (US); Catherina Gomes, Raleigh, NC (US); Ronald Smith, Raleigh, NC (US); Sarah Paluskiewicz, Raleigh, NC (US); Stephen Gray, Raleigh, NC (US); Tyler Confrey-Maloney, Raleigh, NC (US)

(73) Assignee: Undercover Colors, Inc., Raleigh, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/606,119

(22) Filed: May 26, 2017

(65) Prior Publication Data

US 2017/0269108 A1    Sep. 21, 2017

Related U.S. Application Data

(63) Continuation of application No. 15/449,701, filed on Mar. 3, 2017, which is a continuation of application (Continued)

(51) Int. Cl.
*G01N 33/558* (2006.01)
*G01N 33/94* (2006.01)
(Continued)

(52) U.S. Cl.
CPC ........... *G01N 33/94* (2013.01); *G01N 33/146* (2013.01); *G01N 33/54366* (2013.01); *G01N 33/558* (2013.01)

(58) Field of Classification Search
None
See application file for complete search history.

(56) References Cited

U.S. PATENT DOCUMENTS

| 4,826,759 A | 5/1989 | Guire et al. |
| 4,943,522 A | 7/1990 | Eisinger et al. |

(Continued)

FOREIGN PATENT DOCUMENTS

| EP | 0315040 B1 | 1/1993 |
| WO | 2014/184151 A1 | 11/2014 |

(Continued)

OTHER PUBLICATIONS

PCT/US2017/015489, "International Search Report and Written Opinion", dated Apr. 12, 2017, 11 pages.

(Continued)

*Primary Examiner* — Erik B Crawford
(74) *Attorney, Agent, or Firm* — Kilpatrick Townsend & Stockton LLP

(57) ABSTRACT

Described herein are apparatus and methods for detecting substances of abuse or other analytes in liquids. For example, the apparatus and methods described herein can be used for real-time detection of analytes, such as substances of abuse. The methods comprise providing a detection area comprising a chromatographic membrane capable of receiving the liquid and allowing for migration of the liquid, the chromatographic membrane comprising an anti-analyte antibody-particle conjugate, an analyte-conjugate protein at a test line; exposing at least the first location of the apparatus to the liquid; and determining whether an interaction (Continued)

between the analyte-conjugate protein and the liquid occurs to detect the presence of the analyte. The chromatographic membrane may further comprise an anti-species antibody at a control line. Specific buffers are disclosed, and these buffers may be used in the preparation of the apparatus to overcome challenges associated with miniaturization and challenges associated with exposure to beverages.

15 Claims, 6 Drawing Sheets

Related U.S. Application Data

No. 15/508,182, filed as application No. PCT/US2017/015489 on Jan. 27, 2017.

(60) Provisional application No. 62/287,677, filed on Jan. 27, 2016, provisional application No. 62/287,623, filed on Jan. 27, 2016, provisional application No. 62/287,643, filed on Jan. 27, 2016, provisional application No. 62/337,603, filed on May 17, 2016, provisional application No. 62/337,558, filed on May 17, 2016, provisional application No. 62/337,608, filed on May 17, 2016.

(51) Int. Cl.
  *G01N 33/543* (2006.01)
  *G01N 33/14* (2006.01)

(56) References Cited

U.S. PATENT DOCUMENTS

| | | | |
|---|---|---|---|
| 5,267,566 A | 12/1993 | Choucair et al. | |
| 6,022,433 A | 2/2000 | Higuchi et al. | |
| 6,528,323 B1 | 3/2003 | Thayer et al. | |
| 6,551,842 B1 | 4/2003 | Carpenter | |
| 7,148,879 B2 | 12/2006 | Amento et al. | |
| 7,238,533 B1 | 7/2007 | Legge et al. | |
| 7,749,775 B2 | 7/2010 | Maher et al. | |
| 8,003,407 B2 | 8/2011 | Zhou et al. | |
| 8,179,604 B1 | 5/2012 | Prada Gomez et al. | |
| 8,834,946 B2 | 9/2014 | Abramson et al. | |
| 8,895,293 B2 | 11/2014 | Kanaley et al. | |
| 8,920,857 B2 | 12/2014 | Abramson et al. | |
| 9,285,352 B2 | 3/2016 | Abramson et al. | |
| 9,528,973 B2 | 12/2016 | Abramson et al. | |
| 2002/0182600 A1* | 12/2002 | Smith | C07K 14/461 435/6.16 |
| 2005/0043894 A1 | 2/2005 | Fernandez | |
| 2005/0079629 A1 | 4/2005 | Guo et al. | |
| 2006/0019406 A1 | 1/2006 | Wei et al. | |
| 2006/0134611 A1 | 6/2006 | Danzy et al. | |
| 2007/0092977 A1 | 4/2007 | Reich | |
| 2008/0257361 A1 | 10/2008 | Hakim et al. | |
| 2009/0096746 A1 | 4/2009 | Kruse | |
| 2009/0263854 A1 | 10/2009 | Jacono et al. | |
| 2012/0160725 A1 | 6/2012 | Abramson | |
| 2013/0209325 A1* | 8/2013 | Harooni | G01N 21/78 422/400 |
| 2014/0212960 A1 | 7/2014 | Abe et al. | |
| 2014/0228234 A1 | 8/2014 | Zak et al. | |
| 2014/0246037 A1 | 9/2014 | Drake | |
| 2015/0025347 A1 | 1/2015 | Song | |
| 2015/0064800 A1* | 3/2015 | Chance | G01N 33/6863 436/501 |
| 2015/0356669 A1 | 12/2015 | Roescheisen et al. | |
| 2016/0025752 A1* | 1/2016 | Santiago | G01N 21/8483 436/501 |
| 2016/0146773 A1 | 5/2016 | Abramson et al. | |
| 2017/0059542 A1 | 3/2017 | Abramson et al. | |
| 2017/0160253 A1 | 6/2017 | Abramson et al. | |
| 2017/0209313 A1 | 7/2017 | Letourneau et al. | |
| 2017/0242045 A1 | 8/2017 | Letourneau et al. | |

FOREIGN PATENT DOCUMENTS

| | | |
|---|---|---|
| WO | 2015066459 | 5/2015 |
| WO | 2017/132604 A1 | 8/2017 |
| WO | 2017/132614 A1 | 8/2017 |
| WO | 2017/132618 A1 | 8/2017 |

OTHER PUBLICATIONS

PCT/US2017/015500, "International Search Report and Written Opinion", dated Apr. 7, 2017, 9 pages.
PCT/US2017/015504, "International Search Report and Written Opinion", dated Apr. 5, 2017, 9 pages.
Andreou, C., "Microfluidics device detects drugs in saliva fast," 2013, http://www.nanowerk.com/spotlight/spotid=31524.php.
Arce, N., "Meet NailO: MIT's Wearable Device That Turns Fingernail Into Trackpad," 2015, http://www.techtimes.com/articles/47120/20150418/nailo-mits-wearable-device-that-turns-fingernail-into-trackpad.
Bottoms, J., et al., "The Development of Paper Microfluidic Devices for the Presumptive Determination of Seized Drugs," Criminalistics Section, 2015
Chong, H., et al., "Paper-based Microfluidic Point-of-care Diagnostic Devices for Monitoring Drug Metabolism," J Nanomed Biotherapeut Discov, Apr. 25, 2013, https://www.omicsonline.org/paper-based-microfluidic-point-of-care-diagnostic-devices-for-monitoring-drug-metabolism.
Dume, B., "Sweatband measures tiny electrical signals in perspiration," Feb. 2, 2016, http://physicsworld.com/cws/article/news/2016/feb/02/sweatband-measures-tiny-electrical-signals-in-perspiration.
Dume, B., "Tiny sweat sensor goes wireless," Feb. 1, 2016, http://nanotechweb.org/cws/article/tech/63855.
"Fingertip," Digital Trends, http://www.digitaltrends.com/cool-tech/the_next_step_to_our_cyborg_future?_fierce_fabulous_'smart_nails.
Govers III, F, "InTouch tech allows files to be transferred between devices with a touch," 2013, http://newatlas.com/intouch-ring-data-transfer/29486/.
Lopatto, E., "Nail Polish Is the Next Wearable Tech," 2014, http://www.thedailybeast.com/articles/2014/06/04/nail-polish-is-the-next-wearable-tech.
Masterson, A., "In the world of wearable technology, Melbourne nails Shanghai," 2015, http://www.smh.com.au/digital-life-wearables/in-the-world-of-wearable-technology-melbourne-nails-shanghai.
Meinhold, B., "Nail Salons of the Future Offer Wearable-Tech Manicures," 2014 http://www.ecouterre.com/nail_salons_of_the_future_offer_wearable-tech_manicures.
Musile, G., et al., "The development of paper microfluidic devices for presumptive drug detection," Anal. Methods, 2015, https://www.researchgate.net/publications/294891450_The_development_of_paper_microfluidic_devices_for_presumptive_drug_detection.
O'Callaghan, J., "Wearable technology Nailed: Smart fingernails light up when you take a call," 2014 http://www.dailymail.co.uk/sciencetech/article-267522/wearable_technology_nailed:_smart_fingernails_light_up_when_you_take_a_call.
Starr, Michelle, "Fingernail-shaped stylus is manicure-friendly," 2014, https://www.cnet.com/news/fingernail-shaped-stylus-is-manicure-friendly/.
Wang, J., "Tiny Lab Devices Could Attack Huge Problem of Drug-Resistant Infections," Apr. 23, 2015, http://releases.jhu.edu/2015/04/23/tiny-lab-devices-could-attack-huge-problem-of-drug-resistant-infections.
U.S. Appl. No. 15/449,721, Office Action dated Jun. 15, 2017.
"Diafactory Tinea Unguium", Dermatophyte Test Strip, Mar. 8, 2017.
"gRAD One Detection Kit", Bioporto Diagnostics, Nov. 2015.

(56) References Cited

OTHER PUBLICATIONS

"PartoSure Assess the Risk of Preterm Birth", Parsagen Diagnostics, Inc., 2015.
U.S. Appl. No. 15/449,721, Non Final Office Action dated Jun. 15, 2017, 19 pages.

* cited by examiner

METHODS AND APPARATUS FOR DETECTING COMPOUNDS IN LIQUIDS

CROSS-REFERENCE TO PRIORITY APPLICATIONS

This application claims priority to U.S. patent application Ser. No. 15/449,701 filed on Mar. 3, 2017, which claims priority to U.S. patent application Ser. No. 15/508,182 filed on Mar. 2, 2017, which is the U.S. national phase of International Application No. PCT/US2017/15489 filed on Jan. 27, 2017, which application claims priority to U.S. Provisional Application No. 62/287,677 filed on Jan. 27, 2016; U.S. Provisional Application No. 62/287,623, filed on Jan. 27, 2016; U.S. Provisional Application No. 62/287,643, filed on Jan. 27, 2016; U.S. Provisional Application No. 62/337,603, filed on May 17, 2016; U.S. Provisional Application 62/337,558, filed on May 17, 2016; and U.S. Provisional Application 62/337,608, filed on May 17, 2016, each of which is incorporated herein by reference in its entirety.

FIELD

Described herein are apparatus and methods for detecting compounds in liquids. Also described are buffer solutions useful in the apparatus and methods. For example, the apparatus and methods described herein can be used for real-time detection of substances of abuse.

BACKGROUND

The demand and need for persons to be able to detect different substances on a real-time basis has increased with increased frequency of drug use and abuse. In some embodiments, a need may arise to determine if a drug has been added to a beverage without the consumer's knowledge, and to make this determination discretely.

For example, an increased misuse of various psychotropic and/or sedating drugs for recreational or criminal purposes has become more problematic in the present culture. A particularly troubling form of misuse is the surreptitious introduction of these drugs into ordinary beverages for the purpose of rendering the consumer of the beverage disoriented or unconscious. The unknowingly sedated individual may then be taken advantage of, e.g., become the victim of robbery or sexual assault. Drug-facilitated sexual assault has become increasingly common, particularly among younger members of the population, to the degree that most universities have warning and prevention programs and policies in place to prevent drug-facilitated sexual assault. Conventional apparatus to detect such drugs prior to ingestion often are insufficient as they may be too cumbersome to use, take too long to detect the targeted substance, detect only a limited substance, and lack selectivity and sensitivity to many other compounds.

As another example, an increased frequency of diagnoses of auto-immune disorders or highly sensitive allergies has occurred in the general population. For example, Celiac's disease, peanut allergies, lactose allergies or other conditions triggered by different ingested substances have become more common in the general population. If the particular harmful substance is ingested by persons having these types of conditions, significant and severe consequences for the person may result.

In view of these trends, conventional testing methods and devices often are too cumbersome or take too long to evaluate a particular liquid for a targeted substance. In some embodiments, no specific miniaturized apparatus for real-time detection of certain targeted substances or compounds exist. In some embodiments, beverage components may interfere with testing methods.

SUMMARY

The terms "invention", "the invention", "this invention" and "the present invention" used herein are intended to refer broadly to all of the subject matter described herein and the claims below. Statements containing these terms do not to limit the subject matter described herein or limit the meaning or scope of the claims below. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

Disclosed herein are apparatus and methods for detecting the presence of a targeted substance, analyte, or drug in a liquid. In some embodiments, the apparatus is a lateral flow device for a lateral flow assay, whereby a liquid to be analyzed migrates along a fluid path from a sample area, across a conjugate area, across a chromatographic membrane, and into a wick. The target substance or analyte, if present, reacts with an anti-analyte antibody and the reaction results in a visual indication of whether the target analyte is present in the liquid. In some examples, aptamers may be used instead of or in addition to antibodies.

As one example, the methods and apparatus described herein can be used for real-time point-of-contact detection of drugs, such as date rape drugs or other sedating drugs, in beverages or bodily fluids. In other examples, the methods and apparatus described herein can be used for real-time point-of-contact detection of heavy metals in foodstuffs or nutritional supplements; for the detection of contaminants in cosmetics; or for detection of contaminants or nutrients in soils. In some embodiments, the methods and apparatus described herein can be used for real-time detection of any analyte for which an anti-analyte antibody exists or may be manufactured.

Accordingly, described here are viable methods and apparatus for the safe, real-time detection of targeted substances. Examples of such target substances include compounds within abused substances such as drugs, allergens, and biological and environmental toxins. Non-limiting specific examples of target substances include benzodiazepines; amine-containing compounds, including but not limited to, narcotics; alcohol; and other abused drugs, e.g., club drugs. Current "club drugs" include ketamine, 4-hydroxybutanoic acid (GHB), ephedrine, methamphetamine, amphetamine, flunitrazepam, 3,4-methylenedioxy-methamphetamine (MDMA), also known as ecstasy or molly, benzodiazepines such as clonazepam, tetrahydrocannabinol (THC), and many more. Drugs that impair memory or sedating drugs such as zolpidem, eszopiclone, ramelteon, zaleplon, doxepine, triazolam, temazepam, and alprazolam may be detected.

Other examples of such target substances include proteins, sugars, steroids and their metabolites. Still other examples of target substances include poisons, pesticides, toxins, chemical warfare agents, environmental poisons, explosives and the starting materials used to make them. Further, the target substances may include small molecules or mixtures of small molecules. In some embodiments, an apparatus may detect multiple analytes.

Further, a single-analyte or a multi-analyte apparatus may incorporate a signaling mechanism, which in some embodiments is a visual indication, a vibration, or a sound that indicates presence or absence of the target compound. For example, the visual indication can comprise the appearance, or lack thereof, of a colored dot, pattern, or region; the printing of words, such as "SAFE," "OK," "YES," or "NO"; checkmarks; emoticons or symbols such as a "☺"; or fluorescence. In some examples, the signaling mechanism comprises completing lines, logos, patterns or symbols.

In some embodiments, the apparatus described herein are very small. For example, the apparatus may have a length of 20 mm or less, 15 mm or less, 12 mm or 10 mm or less. In some embodiments, the apparatus comprises a length ranging from about 10 mm to about 150 mm, for example, from about 10 mm to about 25 mm, or from about 10 mm to about 20 mm. In some embodiments, the apparatus can have a length of about 10 mm or less, 11 mm or less, 12 mm or less, 13 mm or less, 14 mm or less, 15 mm or less, 16 mm or less, 17 mm or less, 18 mm or less, 19 mm or less, 20 mm or less, 21 mm or less, 22 mm or less, 23 mm or less, 24 mm or less, 25 mm or less, 26 mm or less, 27 mm or less, 28 mm or less, 29 mm or less, or 30 mm or less In some embodiments, the apparatus has a fluid path length greater than the length of the apparatus.

In other embodiments, the apparatus may have other dimensions. The invention, however, overcomes the significant hurdles associated with the miniaturization of lateral flow assay technology. For example, miniaturization can lead to an undesirable increase in the flow rate of the liquid across a chromatographic membrane. In addition to challenges posed by miniaturization, some target liquids (e.g., beverages) include acidic components, high ethanol concentration, high sugar concentrations, and/or other components that may interfere with accurate test results. In some examples, the apparatus is miniaturized to be convenient for discreet use and/or to be wearable. Specific embodiments of wearable apparatus consistent with the present apparatus and methods are described and set forth in a PCT patent application entitled "Wearable Apparatus for Detecting a Target Substance in Liquids," applied for by Undercover Colors, Inc. and filed on the same day as the present application, which is incorporated by reference in its entirety. Additional benefits of miniaturization of a lateral flow assay include reduced raw material usage, the ability to pack more assays into shipping containers, having an increased number of assays multiplexed in a single apparatus, significantly reducing sample volume, and providing rapid test results due to shorter flow distances.

The apparatus and methods described herein overcome challenges associated with miniaturization and challenges associated with exposure to beverages and other mixtures. In some embodiments, the apparatus and methods moderate liquid flow rate by modifying the chromatographic membrane and/or modifying the viscosity of the liquid. In some embodiments, buffer solutions may be used to prepare the apparatus, leaving residual buffer components at desired locations on the apparatus, so that in use the buffer components are reconstituted and neutralize acidic components in a test liquid, slow the progression of the test liquid through the device, or otherwise facilitate the test method. In some embodiments, buffers or buffer solutions may be customized for treatment of various components of an apparatus, such as the sample area, the conjugate area, and/or the chromatographic membrane.

In some embodiments, the buffer solution can comprise a viscosity of at least 2 centiPoise (cP). In some embodiments, the buffer or buffer additives increase the viscosity of the liquid being analyzed, thereby adjusting the flow rate of the liquid across the chromatographic membrane. In some such embodiments, when residual buffer components on an apparatus are reconstituted by a test liquid, the reconstituted buffer solution increases the viscosity of the test liquid and slows the flow rate of the liquid.

In some embodiments, a buffer solution may be utilized in preparing reagents or in applying reagents to the apparatus. In some embodiments, the solution or residual buffer composition may render the test compatible with liquids that may contain an analyte. In some embodiments, unique buffer components may resolve, bind, or eliminate incompatible substances, such as acids (including alpha-hydroxy acids such as lactic acid, malic acid, or citric acid), found in the liquid. In some examples, buffer additives may be introduced to components of the apparatus in a buffer solution or by themselves. In some embodiments, the buffer liquid may be evaporated after the buffer solution is applied. In this case, a residual buffer composition is left on the area of the apparatus that was exposed to the buffer solution.

The sample pad or area, in some embodiments, is the component or portion of the apparatus that is exposed to a test liquid. In some embodiments, a sample pad buffer may neutralize the test liquid when the liquid is an acidic beverage. In some embodiments, the sample pad buffer may comprise salts of weak acids. In some embodiments, the sample pad buffer may be concentrated to provide sufficient neutralization to the beverage, even with a miniaturized sample pad.

In one aspect, a method of detecting an analyte in a liquid described herein comprises the steps of providing an apparatus comprising sample pad, a conjugate pad, and a detection layer, wherein the conjugate pad comprises at least one marker, such as an anti-analyte antibody-particle conjugate, and wherein the detection layer comprises an analyte-conjugate protein and a chromatographic membrane capable of receiving the liquid and allowing for migration of the liquid; exposing at least the sample pad to the liquid; and determining whether an interaction between the analyte-conjugate protein and the liquid occurs to detect the presence of the analyte. In some embodiments, the detection layer further comprises an anti-species antibody. In some embodiments, buffers or buffer solutions may be customized for deposition into or onto the sample pad, conjugate pad, or detection layer. Thus, in some embodiments, the sample pad, conjugate pad, or detection layer comprises residual buffer components. For example, a buffer solution may be deposited onto a detection layer and then dried to form test and/or control lines or areas. In some embodiments, the chromatographic membrane of the detection layer may comprise activated carbon, silica gel, ionic exchange resins, polyelectrolyte polymers, hydrogels, and/or size exclusion chromatography matrices. In some embodiments, the chromatographic membrane may comprise cellulose, nitrocellulose, glass fiber, similar materials or a combination of these materials. For the purposes of this application, "detection layer" and "detection area" may be used interchangeably.

In some embodiments, the marker comprises an anti-analyte antibody conjugated to a particle. In other embodiments, the marker comprises an anti-analyte aptamer conjugated to a particle. For ease of discussion herein the term anti-analyte antibody-particle conjugate may be used to refer to either (or both) anti-analyte antibody-particle conjugates and anti-analyte aptamer-particle conjugates. The particle may be a nanoparticle, microbead, macromolecule, small molecule, or other visualization means. A visualization means may be any composition that contributes to a visible indication when the anti-analyte antibody-particle conjugate experiences an interaction, such as with an analyte-conjugate protein or an anti-species antibody, to develop color at a test or control line. In some examples, the particle is a colored particle, which may be a gold nanoparticle, a magnetic nanoparticle, or a dye-infused polymer microbead. In other embodiments, the particle may be a fluorescent label conjugate, or a radiolabel. Optionally, the particle includes carboxyfluorescein, 2,7-dichlorofluorescein, Eosin B, Eosin Y, erythrosine, fluorescein, fluorescein amidite, fluorescein isocyanate, merbromin, phloxine B, Rose Bengal, derivatives or salts thereof, or combinations thereof. The term anti-analyte antibody-particle conjugate and marker are used interchangeably herein. Unless otherwise specified, either term encompasses conjugates including any suitable particles, such as those listed above. In some embodiments, the marker is present on the conjugate pad, which is generally positioned between the sample pad and the chromatographic membrane.

In some embodiments, the conjugate pad may be pre-treated with a conjugate pad buffer. In some embodiments, the conjugate pad buffer may be quite concentrated because the conjugate pad may be very small, such as 4 mm×4 mm. In some embodiments, the conjugate pad buffer may neutralize compounds found in the liquid that might otherwise interfere with test results. In some examples, the conjugate pad buffer may comprise organic polyols and/or amines, polyelectrolyte polymers, surfactants, and combinations thereof. Further, in some embodiments, the conjugate pad buffer is formulated to be compatible with the anti-analyte antibody-particle conjugate, or in other words, the conjugate pad buffer will not denature the anti-analyte antibody-particle conjugate.

In some embodiments, the anti-analyte antibody-particle conjugate is dissolved in a conjugate dilution buffer before being printed or otherwise deposited on the conjugate pad. For example, the conjugate dilution buffering agent can comprise organic salts, proteins, sugars, and combinations thereof.

In some embodiments, an analyte-conjugated protein deposited on the chromatographic membrane defines a test line or test area, and an anti-species antibody deposited defines a control line or control area. Both the test line and the control line may be immobilized on the chromatographic membrane. As explained further below, the "line" does not have to be linear, and may take various predetermined shapes that inform the user of the presence or absence of the target substance. In some embodiments, the test line or lines define a pattern, which may comprise an indication such as "yes", "no", "safe", "OK", or "☺". In some embodiments, if the pattern has been created to detect multiple analytes, only a certain portion of the pattern may change color. For example, the word "SAFE" may appear as SAFE, where the color of the letter "A" has not developed in the cross-bar region. In some examples, the pattern is formed with a stencil to create letters, symbols, or words. In some examples, the pattern is formed such that the test results complete a design, word, symbol, or number.

In some examples, the liquid comprises a consumable liquid. For example, the consumable liquid can be beer, cider, an energy drink, a flavored drink, a fruit drink, liquor or another alcoholic beverage, milk or a milk-containing beverage, soda, a sports drink, a vegetable drink, water, wine, or a combination thereof. In some examples, the liquid comprises a non-consumable liquid. For example, the non-consumable liquid can be blood, non-potable water, an organic solvent, potable water, serum, treated waste water, untreated waste water, urine, vomit, or a combination thereof. The liquid can comprise a solution, a suspension, or an emulsion. In some embodiments, the liquid comprises solid particles or ice suspended therein. In other embodiments, the liquid is used to extract an analyte from a solid material, such as extracting allergens from non-liquid food products, prior to detection.

In some embodiments, the detection layer is positioned on the surface of an inert substrate. In some examples, the chromatographic membrane may be pretreated with a chromatographic membrane buffering agent, which many interchangeably be called a detection layer buffering agent or a detection area buffering agent. The chromatographic membrane buffering agent may comprise proteins, dibasic sodium phosphate, polyelectrolyte polymers, saccharides, or combinations thereof. In some examples, the chromatographic membrane may be buffered at a pH ranging from 7 to 8.

In another aspect, an apparatus described herein for detecting the presence of an analyte in a liquid comprises a detection layer. In some embodiments, the apparatus comprises a sample pad capable of receiving the liquid, a conjugate pad comprising an anti-analyte antibody-particle conjugate, and a detection layer comprising a chromatographic membrane allowing for migration of the liquid and comprising an analyte-conjugate protein at a test location. In some embodiments, the chromatographic membrane further comprises an anti-species antibody at a control location. In some embodiments, the detection layer further comprises an absorbent, and/or is pre-treated with a desiccant. The absorbent can include chromatography paper, silica gel, or alumina. In some examples, the detection layer comprises a lateral flow assay, which may be multiplexed for testing for the detection of multiple compounds.

In some examples, the sample pad is capable of receiving the liquid, and in some embodiments, the liquid moves from the sample pad to the conjugate pad to the chromatographic membrane. In some embodiments, the liquid moves from the chromatographic membrane to a wick. The wick serves a fluid reservoir to keep fluid from stalling on the chromatographic membrane. In some embodiments, in order to miniaturize the assay, the wick is comprised of a folded layer (e.g., the layer is folded back upon itself). In some embodiments, the wick is U-shaped or S-shaped. In some cases, the fluid path in the apparatus may be curved through multiple planes and/or in multiple directions according to the shape of the components of the apparatus. As a result, in some examples, the overall length of the apparatus may be shortened without impeding the detection ability of the apparatus. In some embodiments, the apparatus has a fluid path length greater than the length of the apparatus.

A particular advantage of miniaturization of a lateral flow assay is timeliness of test results. For example, a conventional lateral flow assay with an 80 mm long chromatographic membrane requires a minimum of 5 minutes to display test results. In contrast, some embodiments of the miniaturized assays described herein display test results much faster. For example, a 12 mm detection layer comprising a residual buffer formulation as described herein requires only about 30 seconds to display test results. An additional advantage of a miniaturized lateral flow assay is reduced test fluid volume. In some examples, a sample volume of no more than 15 µL is required for an apparatus described herein, compared to 80 µL for a conventional 80 mm lateral flow assay. In some embodiments, sample volume is less than 40 µL, less than 30 µL, less than 20 µL, less than 10 µL, or less than 5 µL. In some embodiments test results are displayed in less than 1 minute, less than 30 seconds, less than 15 seconds, less than 10 seconds, or less than 5 seconds.

In some embodiments, the apparatus further comprises a cover over the chromatographic membrane. The cover may comprise one or more openings to permit gas to escape, or the cover may be gas-permeable. In some embodiments, the cover is an opaque cover, a tinted cover, a transparent cover, or a translucent cover. In some embodiments, the cover defines a stencil pattern, which may comprise an indication such as "yes", "no", "safe", "OK", or "☺". The stencil pattern may be placed over the second position of the chromatographic membrane. Such a pattern may be helpful to the user by making the test results easy to understand.

Optionally, the apparatus can be positioned on, within, or below an object. In some embodiments, the object can be a fingernail, an artificial fingernail, a layer of fingernail polish, a fingernail sticker, a fingernail decal, a sticker, a cup, a drink coaster, a drink stirrer, a toothpick, a drink ornament, a pencil, a pen, a ring, a bracelet, a bracelet charm, a necklace, a lanyard pendant, a coaster, a swizzle stick, or another appropriate object. In some embodiments, the apparatus may be positioned on skin or on a fingernail.

In some embodiments, the miniaturized apparatus has a thickness of up to 4 mm. In some embodiments, the length of the apparatus is up to 14 mm. In some examples, the width of the apparatus is up to 4 mm. In some embodiments, the miniaturized apparatus is configured to detect the presence of multiple drugs in many varieties of beer, white wines, red wines, neat liquors, mixed drinks, soda, fruit juices, and water.

In some embodiments, an apparatus for detecting the presence of an analyte in a liquid comprises a conjugate pad comprising a conjugate area comprising at least one anti-analyte antibody-particle conjugate or anti-analyte aptamer-particle conjugate; a detection layer comprising a chromatographic membrane and at least one analyte-conjugate protein, and a sample area for receiving a liquid, wherein the sample area is a separate sample pad or is a portion of the conjugate pad separate from the conjugate area. In some examples, combining the sample pad and conjugate pad into a single membrane reduces the number of components in the apparatus and improves manufacturability, in particular for a miniaturized lateral flow assay apparatus. In some examples, at least one of the detection layer, the sample area, or the conjugate area comprises a residual buffer composition. In other examples, the apparatus comprises a single pad comprising separate areas, such as a sample area, a conjugate area, a detection layer (or chromatographic membrane area), and a wick area. In still other examples, the apparatus comprises a single pad comprising separate areas, such as a sample area, a conjugate area, and a detection layer (or chromatographic membrane area).

In some embodiments, the detection layer further comprises at least one anti-species antibody. In some embodiments, the chromatographic membrane comprises one or more of cellulose, nitrocellulose, polyester fiber, and/or glass fiber. In some embodiments, the apparatus further comprises a cover defining a pattern, wherein the cover is disposed over the detection layer. In some embodiments, the detection layer is positioned on or within or under a natural fingernail, an artificial fingernail, a layer of fingernail polish, a fingernail sticker, a fingernail decal, a sticker, a cup, a drink coaster, a drink stirrer, a toothpick, a drink ornament, a pencil, or a pen.

In some embodiments, the sample area comprises a first residual buffer composition. The first residual buffer composition may comprise a potassium salt of a weak acid and at least one surfactant. In some embodiments, the conjugate area comprises a second residual buffer composition. The second residual buffer composition may comprise a Good's buffer salt and one or more of a protein, an oligomer, a polymer, and a surfactant. In some embodiments, the detection layer comprises a third residual buffer composition. The third residual buffer composition may comprise a phosphate salt and one or more of a saccharide, a protein, an oligomer, and a polymer.

In some embodiments, a method of detecting an analyte in a liquid comprises providing an apparatus as described herein; exposing a portion of the apparatus to the liquid; and observing a visual indication to determine presence or absence of the analyte.

In some embodiments, a method of making an apparatus for detecting the presence of an analyte in a liquid comprises (1) applying a buffer solution to at least one of (a) a conjugate pad comprising a conjugate area comprising at least one anti-analyte antibody-particle conjugate or anti-analyte aptamer-particle conjugate, (b) a detection layer comprising a chromatographic membrane and an analyte-conjugate protein, or (c) a sample area for receiving a liquid, wherein the sample area is a separate sample pad or is a portion of the conjugate pad separate from the conjugate area; (2) drying the buffer solution; and (3) assembling the conjugate pad, detection layer, sample area and a wick so that the sample area is in contact with one portion of the conjugate area, another portion of the conjugate area is in contact with a proximal end of the detection layer, and the wick is in contact with a distal end of the detection layer.

The details of one or more embodiments are set forth in the drawings and description below. Other features, objects, and advantages will be apparent from the drawings, the description, and from the claims.

DETAILED DESCRIPTION

Figure 1:
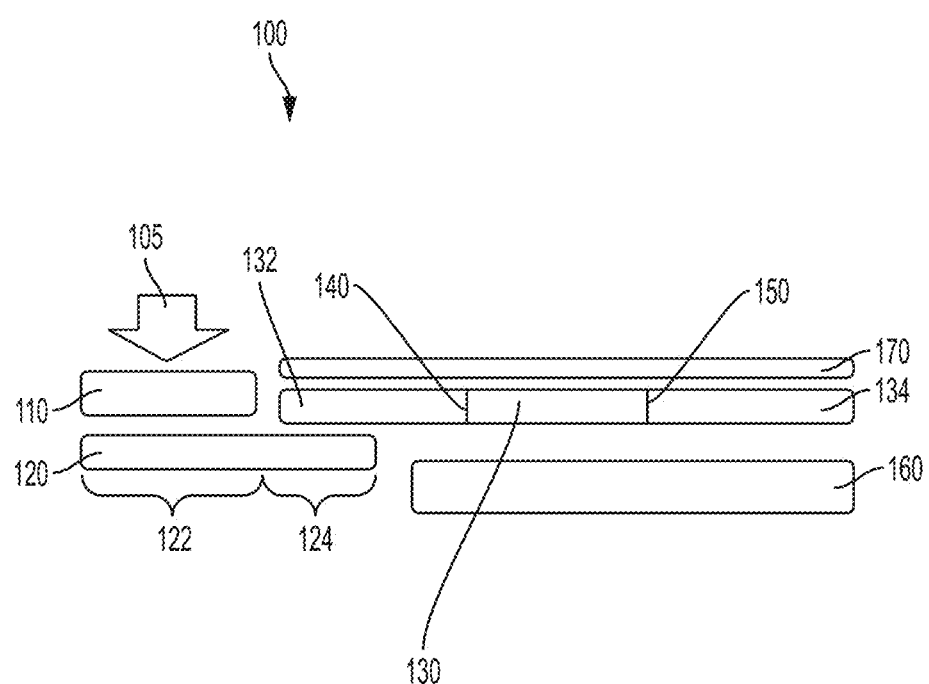
FIG. 1 is an exploded cross-sectional view of an apparatus according to some embodiments described herein.

The subject matter of embodiments of the present invention is described herein with specificity to meet statutory requirements, but this description is not intended to limit the scope of the claims. The claimed subject matter may be embodied in other ways, may include different elements or steps, and/or may be used in conjunction with other existing or future technologies. This description should not be interpreted as implying any particular order or arrangement among or between various steps or elements except when the order of individual steps or arrangement of elements is explicitly described. The illustrative examples are given to introduce the reader to the general subject matter discussed herein and are not intended to limit the scope of the disclosed concepts. The following sections describe various additional embodiments and examples with reference to the drawings in which like numerals indicate like elements and directional descriptions are used to describe illustrative embodiments but, like the illustrative embodiments, should not be used to limit the present invention.

Unless specifically stated to the contrary, the numerical parameters set forth in the following specification are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurements. Moreover, all ranges disclosed herein encompass any and all subranges subsumed therein. For example, a stated range of "1 to 10" includes any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

Described herein are apparatus and methods, and buffer solutions for use therein, for detecting a targeted substance. In some embodiments, the methods and apparatus can detect a targeted compound in a liquid. In some embodiments, the methods and apparatus can detect a targeted substance in a solid. As one example, the methods and apparatus described herein can be used for real-time point-of-contact detection of drugs, such as date rape drugs or other sedating drugs, in beverages or bodily fluids. In other examples, the methods and apparatus described herein can be used for real-time point-of-contact detection of heavy metals in foodstuffs or nutritional supplements, contaminants in cosmetics, contaminants or nutrients in soils, or other analytes of interest. As another example, the methods and apparatus described herein can be used for real-time detection of certain proteins or sugars, e.g., gluten, peanut proteins, or lactose. In some embodiments, the methods and apparatus described herein can be used for real-time detection of other materials, for example, bacteria, pathogens, fungi, metals, or volatile organics and other targeted compounds. In some examples, sedating drugs or date-rape drugs may be detected.

In some embodiments, benzodiazepine drugs may be detected. Benzodiazepines, or "benzos," are a class of drugs having a chemical structure containing a benzene ring fused to a diazepine ring, as shown in formula (1) below. Benzodiazepines have sedating properties, and thus are used by criminals to incapacitate victims.

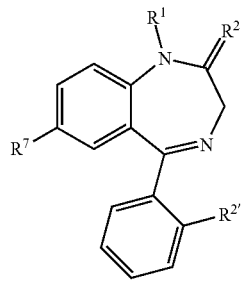

Benzodiazapines that may be detected include, but are not limited to, adinazolam, alprazolam, bentazepam, bretazenil, bromazepam, brotizolam, camezepam, chlordiazepoxide, cinazepam, cinolazepam, clobaxam, clonazepam, chorazepate, clotiazaepam, diazepam, flunitrazepam, lorazepam, lormetazepam, medazepam, midazolam, nitrazepam, oxaepam, temazepam, and thielnalprazolam.

In some embodiments, amine-containing compounds (e.g. amine-containing drugs) may be detected. An "amine-containing" compound or drug, as referred to herein, includes species having at least one primary, secondary, and/or tertiary amine, and/or salts thereof. The amine formula can be represented by $NR^1R^2R^3$, wherein $R^1$, $R^2$, and $R^3$ can be the same or different from one another, and $R^1$, $R^2$ and $R^3$ can include, but are not limited to, hydrogen, substituted or unsubstituted straight-chained or branched $C_1$-$C_6$ alkyls (e.g., methyl, ethyl, propyl, butyl, pentyl, hexyl), substituted or unsubstituted $C_6$-$C_{10}$ aryls (e.g., benzyl), substituted or unsubstituted straight-chained or branched $C_1$-$C_6$ alkanols (e.g., methanol, ethanol, propanol, butanol, pentanol, hexanol), substituted or unsubstituted $C_6$-$C_{10}$ aryl, substituted or unsubstituted heteroaryl, substituted or unsubstituted $C_4$-$C_8$ cycloalkyl, or combinations thereof, with the proviso that $R^1$, $R^2$ and $R^3$ cannot all be hydrogen. The amine salts as described herein can be represented as $(HNR^1R^2R^3)^+X^-$, where $X^-$ is a counterion and $R^1$, $R^2$ and $R^3$ are as defined above for amine. An amine-containing compound as described herein does not include ammonia or uronium compounds or salts thereof, such as urea and derivatives and salts thereof, e.g., urea nitrate.

Examples of amine-containing compounds that may be detected include, for example, amphetamine, cathinone, cyclobenzaprine, diphenhydramine, doxylamine, ephedrine, ketamine, lysergic acid diethylamide (LSD), methamphetamine, 3,4-methylenedioxyamphetamine (MBA), 3,4-methylenedioxy-methamphetamine (MDMA), methcathinone, tetrahydrozoline and salts thereof, and combinations thereof.

In some embodiments, other drugs may be detected by the apparatus and methods described herein. For example, steroids such as estrogens, gestogens, androgens, andrenocortical steroids, bile acids, cardiotonic glycosides and aglycones such as digoxin and digoxigenin, spaonins and sapogenins, their derivatives and metabolites may be detected. Barbiturates such as phenobarbital may be detected. Amphetamines; catecholamines such as ephedrine, L-dopa, epinephrine, carcene, papverin; and metabolites thereof may be detected. Alkaloids such as morphine alkaloids may be detected. Purines such as theophylline, caffeine, and metabolites and derivative thereof may be detected. Marijuana derivatives such as cannabinol and tetrahydrocannabinol may be detected. Vitamins such as A, B (such as $B_{12}$), C, D, E, K, folic acid and thiamine may be detected. Drugs that impair memory or sedating drugs such as zolpidem, eszopiclone, ramelteon, zaleplon, doxepine, triazolam, temazepam, and alprazolam may be detected. Antibiotics such as penicillin, chloromycetin, actinomycetin, tetracycline, terramycin, and metabolites and derivative thereof may be detected. In addition, antihistamines, methadone, and other drugs may be detected.

The apparatus and methods described herein can detect a target substance in a liquid. The liquid may comprise a solution, a suspension, or an emulsion. In some examples, the liquid has solid particles or ice suspended therein.

In some embodiments, the liquid comprises a consumable liquid. For example, the consumable liquid can include beer, cider, energy drinks, flavored drinks, fruit drinks, liquor or other alcoholic beverages, milk, milk-containing beverages, soda, sports drinks, vegetable drinks, water, wine, or combinations thereof. In some embodiments, the liquid has a high concentration of ethanol. In some embodiments, the liquid has a high concentration of sugar. In some embodiments, the liquid is acidic.

In some examples, the liquid comprises a non-consumable liquid. For example, the non-consumable liquid can include blood, non-potable water, organic solvents, potable water, serum, treated waste water, untreated waste water, urine, vomit, sweat, tears, reproductive fluids, other bodily secretions, or combinations thereof.

If the desired targeted substance is suspected to be in a non-liquid, for example, in a solid food, a suitable solvent may be used to extract at least some of the targeted substance, and that solvent may serve as the liquid tested using apparatus and methods described herein. Similarly, nutritional supplements, cosmetics, or soil may be tested for presence of heavy metals or undesirable chemicals by contacting the solid with a solvent to extract any target analyte and testing the solvent. Further, soluble air quality contaminants may be extracted for testing. In some examples, the extraction employs a solvent or water.

The apparatus and methods described herein can provide preliminary forensic analyses that can be of assistance to law enforcement or forensic experts, for example, by providing quick confirmation of the presence or absence of a targeted analyte in the blood, sweat, tears, urine, vomit, or beverage of a person who may have ingested a target compound. Advantageously, the apparatus and methods described herein allow for real-time determination of any of the above-mentioned analytes. The methods described herein require no expensive equipment or scientific training to identify presence or absence of an analyte.

In some embodiments, an apparatus according to embodiments described herein is a lateral flow device for a lateral flow assay, whereby a liquid being analyzed migrates along a fluid path from a sample area, across a conjugate area, and then across a chromatographic membrane to a wick. The target substance or analyte, if present, reacts with an anti-analyte antibody, and the reaction results in a visual indication of whether the target analyte is present in the liquid.

I. Buffer Solutions

Buffer solutions described herein may be applied to parts of a lateral flow apparatus as described herein to enhance performance of the apparatus. For example, a buffer solution may render a test apparatus and method as described herein compatible with liquids that contain components that otherwise would interfere with the analysis. Buffer solutions may also be used to slow liquid travel time across a membrane to ensure sufficient reaction time between any target analyte and a corresponding anti-analyte antibody or analyte-conjugate protein.

The buffer solutions described herein include salts, acids, proteins, excipients, viscosity modifiers, and/or surfactants. In this application, "buffer," "buffer solution," and "buffer formulation" may be used interchangeably to describe a solution comprising at least one buffering compound and water. Optionally, the buffer solution may further comprise buffer additives. Buffer additives are compounds that do not necessarily contribute to the buffering ability of the buffer solution (e.g., they do not substantially affect the acid-base chemistry of the buffer solution). In some embodiments, the buffering compounds may comprise buffer salts and optionally additional acids or bases, such as hydrochloric acid or sodium hydroxide. In some embodiments, buffer additives comprise shielding agents such as proteins, e.g. Bovine Serum Abumin (BSA); viscosity modifying polymers such as poly(vinyl alcohol) (PVA), poly(vinyl pyrrolidone) (PVP), poly(ethylene glycol) (PEG), or oligomers or copolymers thereof; excipients or stabilizing agents such as saccharides (for example, dextran, trehalose, maltodextrose); and surfactants such as non-ionic surfactants (for example, polysorbate 20 or 80, Triton X-100, Triton X-305, or Pluronic F-68).

Buffer salts useful in the buffer solutions described herein include weak acids and bases. The buffer salts may be mono-basic, di-basic, tri-basic, or have higher-order basicity, depending on how many protons the buffer salt can accept. For example, a mono-basic buffer salt will be able to accept one proton, whereas a di-basic buffer salt can accept two protons. Similarly, acids useful in the buffer solutions described herein can be mono-protic, di-protic, tri-protic, and so on, depending on how many protons they can donate.

Traditional buffering acids and bases, such as boric acid, carbonic acid, and phosphoric acid, and their corresponding borate, carbonate, and phosphate salts may be used in the buffer solutions described herein. In addition, Good's buffer salts, as described by Norman Good and colleagues, and similar salts commonly used in biochemical applications may also be used. Non-limiting examples of buffer salts useful in the buffer solutions described herein are monosodium phosphate, disodium phosphate, sodium tetraborate, tris(hydroxymethyl)methylaminopropanesulfonic (TAPS), N-cyclohexyl-2-aminoethanesulfonic acid (CHES), N-tris(hydroxymethyl)methyl-4-aminobutanesulfonic acid (TABS), bis-tris methane (Bis TRIS), tris(hydroxymethyl)aminomethane (TRIS), 2-[[1,3-dihydroxy-2-(hydroxymethyl)propan-2-yl]amino]ethanesulfonic acid (TES), 2-(N-morpholino)ethanesulfonic acid (MES), N-(carbamoylmethyl)iminodiacetic acid (ADA), N-(2-acetamido)-2-aminoethanesulfonic acid (ACES), Bis tris propane, piperazine-N,N'-bis(2-ethanesulfonic acid)(PIPES), N-(2-acetamido)-2-aminoethanesulfonic acid (ACES), 3-morpholino-2-hydroxypropanesulfonic acid (MOPSO), cholamine chloride, (3-(N-morpholino)propanesulfonic acid) (MOPS), N,N-bis(2-hydroxyethyl)taurine (BES), N,N-bis(2-hydroxyethyl)-3-amino-2-hydroxypropanesulfonic acid (DIPSO), 4-(N-morpholino)butanesulfonic acid (MOBS), 3-[N-tris(hydroxymethyl)methylamino]-2-hydroxypropanesulfonic acid (TAPSO), acetamidoglycine, triethanolamine(TEA), piperazine-N,N'-bis(2-hydroxypropanesulfonic acid) POPSO, 4-(2-hydroxyethyl)piperazine-1-(2-hydroxypropanesulfonic acid) hydrate (HEPPSO), 3-[4-(2-hydroxyethyl)-1-piperazinyl]propanesulfonic acid (HEPPS), tricine, tris(hydroxymethyl)aminomethane, trometamol (TRIZMA), glycinamide, glycyl-glysine, N-(2-hydroxyethyl)piperazine-N'-(4-butanesulfonic acid) (HEPBS), bicine, 2-amino-2-methyl-1-propanol (AMP), N-(1,1-dimethyl-2-hydroxyethyl)-3-amino-2-hydroxypropanesulfonic acid (AMPSO), N-cyclohexyl-2-hydroxyl-3-aminopropanesulfonic acid (CAPSO), N-cyclohexyl-3-aminopropanesulfonic acid (CAPS), 4-(cyclohexylamino)-1-butanesulfonic acid (CABS), and (4-(2-hydroxyethyl)-1-piperazineethanesulfonic acid) (HEPES). Other potentially useful buffer salts are salts of amino acids such as: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine. Further, buffer salts could include carnitine, gamma-aminobutyric acid, taurine.

The following examples disclose buffering compounds according to some embodiments. In some examples, a buffer solution comprises TRIS (tris(hydroxymethyl)aminomethane) and water. The concentration of TRIS in the buffer solution can be up to 0.3 M, up to 0.4 M, up to 0.5 M, up to 0.60 M, up to 0.7 M, up to 0.8 M, or up to 1.0 M. In some embodiments the TRIS concentration is about 0.5 M.

In some embodiments, a buffer solution useful in the methods and apparatus described herein comprises a dibasic salt, a monobasic salt, and water. In some embodiments, the dibasic salt and monobasic salt have a common anion. For example, the common anion may be a phosphate anion, although any other known dibasic anion may be used. The cation may be any monovalent or divalent cation, such as potassium, sodium, or calcium. In some examples, the buffer solution comprises sodium phosphate monobasic and/or sodium phosphate dibasic.

In other embodiments, a buffer solution useful in the methods and apparatus described herein comprises one or more phosphate salts, one or more chloride salts, or a combination thereof, and water. Examples of useful chloride salts include sodium chloride and/or potassium chloride. Optionally, the one or more phosphate salts include disodium phosphate and/or potassium dihydrogen phosphate. Optionally, the salts used to prepare the phosphate buffer solution are hydrates. The hydrate may be, for example, a monohydrate, a dihydrate, a trihydrate, a tetrahydrate, a pentahydrate, a hexahydrate, or a heptahydrate. In some embodiments, the disodium phosphate used to prepare the phosphate buffer may be disodium phosphate heptahydrate ($Na_2HPO_4 \cdot 7H_2O$). A phosphate salt may be present in the buffer in an amount of up to 25 mM, up to 25 mM, up to 50 mM, up to 100 mM, up to about 200 mM, from about 5 to about 15 mL, from about 20 to about 25 mM, from about 40 to about 60 mM, or from about 80 to about 120 mM.

In some embodiments a buffer solution useful in the methods and apparatus described herein comprises a borate salt and water. Optionally, the borate salt is a hydrate. As described above, the hydrate may be, for example, a monohydrate, a dihydrate, a trihydrate, a tetrahydrate, a pentahydrate, a hexahydrate, or a heptahydrate. For example, the borate salt used to prepare the borate buffers can be tetraborate heptahydrate ($Na_2B_4O_7 \cdot 10H_2O$). Borate salts may be present in the buffer in amounts of up to 25 millimolar, up to 50 mM, or up to 100 mM.

In some embodiments, a buffer solution useful in the methods and apparatus described herein comprises one or more carboxylates such as succinate and citrate and water. In some embodiments, a buffer solution comprises a monovalent cation carbonate, such as potassium carbonate ($K_2CO_3$) or divalent cation carbonate, such as calcium carbonate ($CaCO_3$). For example, potassium carbonate may be present in the buffer solution in amounts of up to 500 mM, up to 750 mM, up to 1.0 M, up to 1.1 M, up to 1.2 M, up to 1.3 M, up to 1.4 M, or up to 1.5 M.

In some embodiments, a buffer solution useful in the apparatus and methods described herein includes acids or bases in addition to any weak acid or base buffering compounds. These additional acids and bases may be used to adjust the final pH of the buffered solutions. In some embodiments, hydrochloric acid (HCl) or sodium hydroxide (NaOH) may be used as such additional acid or base, although other acids or bases could be used instead.

The following examples disclose buffer additives according to some embodiments. In some embodiments, a buffer solution useful in the methods and apparatus described herein may include one or more shielding agents. In some embodiments a shielding agent is a protein. Non-limiting examples of shielding agents include gelatin, casein, and Bovine Serum Albumin (BSA). In some examples, a buffer solution may comprise BSA in any amount from less than 1 percent to more than 10 percent based on the weight of the buffer solution. In some embodiments, the buffer solution comprises BSA in about 0.1%, about 0.2 wt %, about 0.5 wt %, about 1 wt %, about 3 wt %, about 5 wt %, about 8 wt %, about 10 wt %, about 12 wt %, or about 15 wt % based on the weight of the buffer solution.

In some embodiments, a buffer solution useful in the apparatus and methods provided herein may include at least one excipient (e.g., one, two, three, four, or more excipients). Useful excipients include, but are not limited to, saccharides and amino acids. Useful saccharides include, for example, monosaccharides and disaccharides, such as but not limited to sucrose, mannitol, sorbitol, lactose, dextrose, fructose, glucose, maltose and combinations thereof. In some examples, the buffers are substantially free of saccharides other than sucrose (for example, the buffers are substantially free of non-sucrose polyols). Substantially free of non-sucrose polyols means including less than 0.1%, less than 0.01%, less than 0.001%, less than 0.0001%, or 0% of non-sucrose polyols based on the weight of the buffer.

In some embodiments, buffer solutions useful in the apparatus and methods provided herein comprise viscosity modifiers. Suitable viscosity modifiers include, but are not limited to, saccharides, such as sucrose, and polymers, such as poly(vinyl alcohol) (PVA), poly(vinyl pyrrolidone) (PVP), poly(ethylene glycol) (PEG), or oligomers or copolymers thereof. Any molecular weight polymer or oligomer may be used, provided the polymer or oligomer is soluble in the buffer solution. In some embodiments, poly(vinylpyrrolidone)-40 (PVP-40) is used to increase the viscosity of the buffer solution. In some embodiments, the viscosity modifier is present at up to 0.1 wt %, up to 0.2 wt %, up to 0.3 wt %, up to 0.4 wt %, up to 0.5 wt %, up to 0.6 wt %, up to 0.7 wt %, up to 0.8 wt %, up to 0.9 wt %, up to 1.0 wt %, up to 2.0 wt %, up to 3.0 wt %, up to 4.0 wt %, or up to 5.0 wt % based on the total weight of the buffer solution.

In some embodiments, buffer solutions useful in the apparatus and methods provided herein comprise at least one detergent or surfactant. Detergent and surfactant refer to a substance having both a hydrophilic moiety and a hydrophobic moiety. Useful surfactants include ionic and non-ionic surfactants. In some examples, Triton X-35, Triton X-100, and/or Pluronic F-68 is optionally included as the non-ionic surfactant in a buffer solution. One or more surfactants can be present in the buffers, optionally in an amount of less than 1% by weight based on the weight of the buffer. For example, the surfactant(s) can be present in the buffers in an amount of up to 3%, up to 2%, up to 1%, up to 0.75%, up to 0.5% by weight, up to 0.25% by weight, up to 0.1% by weight, or up to 0.05% by weight (e.g., 0.25% by weight or 0.5% by weight).

In some embodiments, the surfactant may be one or more non-ionic surfactant such as fatty alcohols, polyethylene glycol alkyl ethers, polypropylene glycol alkyl ethers, glucoside alkyl ethers, polyethylene glycol octyl, glycerol alkyl esters, phenyl ethers (such as Triton X-100), polyoxyethylene (20) oleyl ether (such as Brig 98), octylphenol ethoxylate (such as Triton X-305), polyethylene glycol alkylphenyl ethers, polyethoxylated tallow amine, N,N-bis[3-(D-gluconamido)propyl]cholamide, polyoxyethylene (20) cetyl ether, dimethyldecylphosphine oxide, branched octylphenoxy poly(ethyleneoxy)ethanol, a polyoxyethylene-polyoxypropylene block copolymer, t-octylphenoxypolyethoxyethanol, polyoxyethylene (20) sorbitan monooleate, alkyl polyglycosides, polysorbates (such and Tween), or poloxamers (such Synperonics, Pluronics, or Kolliphor).

In some embodiments, the surfactant may be an anionic surfactant such as 2-acrylamido-2-methylpropane sulfonic acid, ammonium lauryl sulfate, ammonium perfluorononanoate, docusate, perfluorobutanesulfonic acid, perfluorononanoic acid, perfluorooctanesulfonic acid, perfluorooctanoic acid, sodium alkyl sulfate, sodium dodecyl sulfate, sodium dodecylbenzenesulfonate, sodium laurate, sodium laureth sulfate, sodium lauroyl sarcosinate, sodium myreth sulfate, sodium nonanoyloxybenzenesulfonate, sodium pareth sulfate, or sodium stearate.

In some embodiments, the surfactant may be a cationic surfactant such as behentrimonium chloride, benzalkonium chloride, benzethonium chloride, cetrimonium bromide, cetrimonium chloride, dimethyldioctadecylammonium bromide, dimethyldioctadecylammonium chloride, lauryl methyl gluceth-10 hydroxypropyl dimonium chloride, octenidine dihydrochloride, N-oleyl-1,3-propanediamine, stearalkonium chloride, or tetramethylammonium hydroxide.

In some embodiments, the surfactant may be a zwitterionic surfactant such as CHAPS detergent, cocamidopropyl betaine, cocamidopropyl hydroxylsultaine, lauryldimethylamine oxide, and Sodium lauroamphoacetate. These surfactant examples are non-limiting, as other nonionic, anionic, cationic, or zwitterionic surfactants may be used.

Buffer solutions provided herein may be used to pretreat one or more specific areas of an apparatus to deposit buffering compounds and buffer additives in one or more desired locations of the apparatus. In some embodiments, a buffer solution is applied to the respective portion of the apparatus as a solution or suspension, then the liquid portion of the buffer solution is removed (e.g. by evaporation) leaving a residual buffer component comprising one or more residual buffering compounds and, any residual buffer additives present in the buffer solution. The residual buffer component includes any buffer components that remain after the liquid medium (e.g. water) is removed. As a test liquid traverses the apparatus, it comes into contact with the deposited buffer components and any residual buffer additive and dissolves them, essentially reconstituting the buffer solution. The term "reconstituted" does not imply that the buffer solution formed in the test liquid has the same concentration as the buffer solution used to pre-treat the apparatus or that the solutions are identical. The reconstituted buffer solution may have a different concentration than the buffer solution used to pre-treat the apparatus.

For example, a first buffer solution may be applied to a sample area to deposit buffering compounds and buffer additives selected to neutralize or counteract beverage components that might interfere with a test result. Another buffer solution may be applied to the chromatographic membrane to increase the viscosity of the beverage or liquid, for example to slow its migration across the chromatographic membrane. In some embodiments specific combinations of buffer solutions may be used in an apparatus where a first buffer solution is applied to the sample area, a second buffer solution is applied to the chromatographic membrane, and the first and second buffer solutions are different. Such combinations of buffer solutions can be used synergistically to improve the performance of the apparatus and methods across a wide range of test liquids.

In some embodiments, specific combinations of neutralizing agents, buffering agents, and surfactants are used synergistically to improve the performance of the assay across a wide range of sample matrices. Neutralizing agents can be used alone or in combination with buffering agents to improve assay performance across a diverse set of test liquids. Neutralizing reagents may include traditional buffering agents, such as Good's buffer salts, and other acidic or basic components which treat the sample prior to the sample encountering the detection means. Neutralizing reagents may consist of carboxylate salts such as sodium citrate or potassium carbonate. Buffering reagents create a stable and consistent environment for the detection means to function within and may consist of ionic or zwitterionic buffer salts. Buffering agents alone may not provide adequate neutralization of all sample types. Neutralizing agents alone may be too acidic or basic to be compatible with the detection means. For example, one potential combination of neutralizing agent and buffering agent is potassium carbonate (0.1 to 3M) and tris (0.1M to 3M), respectively, at any combination of neutralizing and buffering agent concentrations within the specified ranges. In some embodiments, the ratio of neutralizing agent to buffering agent is 2:1.

The neutralizing agent may be located in an assay component such as the sample pad or area which is separate from the buffering agent located in the conjugate pad or area. In some cases, the neutralizing agent is $K_2CO_3$ (0.1 to 3M) or other carboxylate salt. In some cases, the buffering agent is Tris (0.1M to 3M) or other Good's buffer agent. Separation of the neutralizing agent from the conjugate pad is of particular importance when the neutralizing agent is not compatible with the antibody-particle conjugate as is the case with $K_2CO_3$ and antibody-gold nanoparticle conjugates. The neutralizing agent may deposited on the same assay component but in a separate area from the detection means. In some cases, the neutralizing agent is $K_2CO_3$ (0.1 to 3M) or other carboxylate salt. In some cases, the buffering agent is Tris (0.1M to 3M) or other Good's buffer agent.

In some embodiments, certain combinations of non-ionic surfactants are particularly useful for ensuring an apparatus described herein is compatibile with a wide range of test liquids. These non-ionic surfactants may be used alone or in conjugation with neutralizing and buffering agents. In some examples, a first non-ionic surfactant is Pluronic F68 (0.1% to 2%) or other poloxamer and a second non-ionic surfactant is Triton X-100 (0.1% to 2%) or other polyethylene oxide phenyl ether at any combination of concentrations within the stated ranges for each compound. Buffer formulations and residual buffer formulation may comprise a first and a second non-ionic surfactant at any combination of concentrations within the stated ranges for each surfactant. The non-ionic surfactants may be located in the conjugate pad. The non-ionic surfactants may be located in the sample pad. One non-ionic surfactant may be located in the sample pad and one non-ionic surfactant may be located in the conjugate pad.

In some embodiments, combinations of neutralizing agents, buffering agents, and non-ionic surfactants were found to improve assay performance. For example, a useful combination includes the neutralizing agent K2CO3 (0.1 to 3M), buffering agent Tris (0.1M to 3M), the non-ionic surfactant Triton X-100 (0.1 to 2%), and a second non-ionic surfactant Pluronic F68.

In some embodiments a buffer solution described herein comprises a dibasic salt and water. In some embodiments, the buffer solution comprises sodium phosphate monobasic and sodium phosphate dibasic. In one specific example, a buffer solution comprises sodium phosphate monobasic in an amount of 5-20 grams per liter and sodium phosphate dibasic in an amount of 540-80 grams per liter. In some embodiments, the water is molecular biology reagent grade water. The buffer solution is prepared by placing 0.7-0.9 liter of water in a container, adding the prescribed amounts of monobasic and dibasic salts, and then adding water to one liter. The pH of the buffer solution is adjusted to the desired pH using NaOH or HCl as needed, and the buffer solution is filtered using a micron filter.

In some embodiments, the monobasic salt may be present in 11.4, 11.2, 11.0, 10.8, 10.6, 10.4, 10.2, 10.0, 9.8, 9.6, 9.4, or 9.2 grams times the batch volume. In some embodiments, the dibasic salt may be present in 70, 65, 60, 55, 50, or 45 grams times the batch volume. If salts other than sodium phosphate monobasic and sodium phosphate dibasic are used, these amounts may be adjusted as understood by one of skill in the art. In some embodiments, the buffer solution has a pH of 7.3, 7.4, 7.5, 7.6, 7.7, or 7.8, or any number in this range. A sodium phosphate monobasic/sodium phosphate dibasic buffer solution is useful for applying reagents to an apparatus. Specifically, in some embodiments, a sodium phosphate monobasic/sodium phosphate dibasic buffer solution may be used as an elution buffer to desalt an antibody that has been stored.

A buffer solution described herein may comprise a borate salt, boric acid, and water. In some embodiments, the buffer solution may comprise a borate salt, boric acid, BSA, water, and optionally sodium hydroxide or hydrochloric acid. In some examples, the buffer solution comprises sodium tetraborate decahydrate in an amount of 5-20 grams per liter of buffer solution and boric acid in an amount of 0.5-2 grams per liter of buffer solution. In some embodiments, BSA is present in an amount of 5-20 grams per liter of buffer solution. In some embodiments, the water is molecular biology reagent grade water. In some embodiments, the buffer solution is prepared by measuring the dry reagents into a container, and adding water to final volume. In some embodiments, the pH of the buffer solution is adjusted to the desired pH using NaOH or HCl as needed. In some examples the buffer solution is filtered using a 0.2 micron filter.

In some embodiments, the sodium tetraborate decahydrate may be present in 16, 14, 12, 11.8, 11.6, 11.4, 11.2, 11.0, 10, 9, or 8 grams per liter of buffer solution, or any number within this range. In embodiments, the boric acid may be present in 2.0, 1.8, 1.6, 1.4, 1.2, 1.0, 0.8, 0.6, or 0.4 grams per liter of buffer solution, or any number within this range. In some examples, BSA may be present at 12, 11, 10, 9, or 8 grams per liter of buffer solution. In some embodiments, the buffer solution has a pH of 9.5, 9.4, 9.3, 9.2, 9.1, 9.0, 8.9, 8.8, 8.7, 8.6, or 8.5, or any number within this range. This borate buffer solution is useful for applying reagents to an apparatus. Specifically, in some embodiments, this borate buffer solution may be used as a conjugation blocking buffer in the preparation of an antibody-particle conjugate.

A buffer solution described herein may comprise a borate salt, boric acid, and water. In some embodiments, the buffer solution may comprise borate salt, boric acid, BSA, water, and optionally sodium hydroxide or hydrochloric acid. In some examples, the buffer solution comprises sodium tetraborate decahydrate in an amount of 5-20 grams per liter of buffer solution and boric acid in an amount of 0.5-20 grams per liter of buffer solution. In some embodiments, BSA is added in an amount of 50-200 grams per liter of buffer solution. In some embodiments, the water is molecular biology reagent grade water. In some embodiments, the buffer solution is prepared by measuring the dry reagents into a container, and adding water to final volume. In some embodiments, the pH of the buffer solution is adjusted to the desired pH using NaOH or HCl as needed. In some examples the buffer solution is filtered using a 0.2 micron filter.

Other borate buffers comprising different concentrations of BSA may also be useful. In other embodiments, the sodium tetraborate decahydrate may be present in 16, 14, 12, 11.8, 11.6, 11.4, 11.2, 11.0, 10, 9, or 8 grams per liter of buffer solution. In some other embodiments, the boric acid may be present in 2.0, 1.8, 1.6, 1.4, 1.2, 1.0, 0.8, 0.6, or 0.4 grams per liter of buffer solution, or any number within this range. In some other examples, BSA may be present at 120, 110, 100, 90, or 80 grams per liter of buffer solution. In some other embodiments, the buffer solution has a pH of 9.5, 9.4, 9.3, 9.2, 9.1, 9.0, 8.9, 8.8, 8.7, 8.6, or 8.5, or any number within this range. This other borate buffer solution is useful for applying reagents to an apparatus. Specifically, in some embodiments, this buffer solution may be used as a conjugate dilution buffer in applying an antibody-particle conjugate to an apparatus.

A buffer solution described herein may comprise a dibasic salt and water. In some embodiments, a useful buffer solution comprises sodium phosphate monobasic and sodium phosphate dibasic; one or more of a saccharide, a protein, and a viscosity modifier; one or more of sucrose, BSA, and poly(vinylpyrrolidone)-40 (PVP-40); and optionally sodium hydroxide or hydrochloric acid. In some examples, the buffer solution comprises sodium phosphate monobasic in an amount of 0.1-0.5 grams per liter of buffer solution and sodium phosphate dibasic in an amount of 0.5-3 grams per liter of buffer solution. In some examples, the buffer solution further comprises 0.5-2 g sucrose per liter of buffer solution, 0.5-2 g BSA per liter of buffer solution, and 1-5 g PVP-40 per liter of buffer solution. In some embodiments, the water is molecular biology reagent grade water. In some embodiments, the buffer solution is prepared by adding the prescribed amounts of monobasic and dibasic salts, adding the sucrose, BSA, and PVP-40, and then adding water to final volume. In some embodiments, the pH of the buffer solution is adjusted to the desired pH using NaOH or HCl as needed. In some examples the buffer solution is filtered using a 0.2 micron filter.

In some embodiments, the monobasic salt may be present in 0.3, 0.2, or 0.1 grams per liter of buffer solution. In some embodiments, the dibasic salt may be present in 2, 1.8, 1.6, 1.4, 1.2, 0.8, 0.6, or 0.5 grams per liter of buffer solution. If salts other than sodium phosphate monobasic and sodium phosphate dibasic are used, these amounts may be adjusted as understood by one of skill in the art. Sucrose may be present in 2, 1, or 0.5 grams per liter of buffer solution. BSA may be present in 2, 1, or 0.5 grams per liter of buffer solution. PVP-40 may be present in 4, 2, or 1 grams per liter of buffer solution. In some embodiments, the buffer solution has a pH of 7.3, 7.4, 7.5, 7.6, 7.7, or 7.8, or any number in this range. This buffer solution is useful for slowing the flow of a liquid in an apparatus. Specifically, in some embodiments, this buffer solution may be used as a pretreatment buffer solution for a chromatographic membrane in an apparatus.

A buffer solution described herein may comprise a Good's buffer salt and water. In some embodiments a buffer solution comprises a Good's buffer salt, a protein, a viscosity modifier, optionally one or more surfactants, and optionally one or more additional acids or bases. In some examples, the buffer solution comprises TRIS. In some embodiments, the buffer solution comprises TRIS, BSA, PVP-40, optionally one or more of Triton X-100 and Pluronic F-68, optionally sodium hydroxide or hydrochloric acid. In some examples, the buffer solution comprises TRIS in an amount of 50-200 grams per liter of buffer solution. In some examples, the buffer solution further comprises 20-40 g BSA per liter of buffer solution, and 5-20 g PVP-40 per liter of buffer solution. In some embodiments, the buffer solution further comprises 1-5 g Triton X-100 per liter of buffer solution and 2-10 g Pluronic F-68 per liter of buffer solution. In some embodiments, the water is molecular biology reagent grade water. In some embodiments, the buffer solution is prepared by adding the prescribed amounts of TRIS, adding the BSA, and PVP-40, Triton X-100 and Pluronic F-68, and then adding water to final volume. In some embodiments, the pH of the buffer solution is adjusted to the desired pH using NaOH or HCl as needed. In some examples the buffer solution is filtered using a 0.2 micron filter.

In some embodiments, the TRIS may be present in about 150, 140, 130, 120, 115, 110, 100, 90, or 80 grams per liter of buffer solution. BSA may be present in 40, 35, 32, 30, 28 or 25 grams per liter of buffer solution. PVP-40 may be present in about 20, 15, 12, 10, 8 or 55 grams per liter of buffer solution. Triton X-100 may be present in about 5, 4, 3, 2.8, 2.5, 2.3, or 2 grams per liter of buffer solution. Pluronic F-68 may be present in about 8, 7, 6, 5.5, 5, 4.5, 4, 3.5, 3, or 2 grams per liter of buffer solution. In some embodiments, the buffer solution has a pH of 7.6, 7.8, 8.0, 8.2, or 8.4, or any number in this range. This buffer solution is useful for pretreating a component of an apparatus. Specifically, in some embodiments, this buffer solution may be used as a pretreatment buffer solution for a conjugate pad in an apparatus.

A buffer solution described herein may comprise a carboxylate and water. In some examples, the buffer solution comprises potassium carbonate. Optionally, the buffer solution may comprise one or more surfactants. In some embodiments, the buffer solution comprises a carboxylate (such as potassium carbonate), water, optionally one or more surfactants, and optionally one or more additional acids or bases. In some embodiments, the surfactant is Triton X-305. In some examples, the buffer solution comprises potassium carbonate in an amount of 50-200 grams per liter of buffer solution. In some examples, the buffer solution further comprises 1-10 g Triton X-305 per liter of buffer solution. In some embodiments, the water is molecular biology reagent grade water. In some embodiments, the buffer solution is prepared by adding the prescribed amounts of potassium carbonate and Triton X-305 to a container, and then adding water to final volume. In some embodiments, the pH of the buffer solution is adjusted to the desired pH using NaOH or HCl as needed. In some examples the buffer solution is filtered using a 0.2 micron filter.

In some embodiments, the potassium carbonate may be present in about 150, 140, 138, 136, 130, 120, 110, 100, or 80 grams per liter of buffer solution. Triton X-100 may be present in about 5, 4, 3.8, 3.6, 3.4, 3, 2.5, or 2 grams per liter of buffer solution. In some embodiments, the buffer solution has a pH of 7.4, 7.2, 7.0, 6.8, or 4.4, or any number in this range. This buffer solution is useful for pretreating a component of an apparatus. Specifically, in some embodiments, this buffer solution may be used as a pretreatment buffer solution for a sample pad in an apparatus.

II. Methods of Detecting Targeted Compounds

Methods of detecting targeted compounds, including substances of abuse and/or drugs, are described herein.

Examples of non-limiting methods of detecting an analyte according to embodiments described herein include providing an apparatus comprising a sample pad, a conjugate pad, a detection layer comprising a chromatographic membrane, and a wick. The apparatus is described in greater detail in Section III. The chromatographic membrane of the invention is capable of receiving the liquid being tested and also allows for migration of the liquid through the chromatographic membrane, in some embodiments by capillary action. The sample pad is exposed to the liquid, for example by direct contact with the liquid, the liquid migrates from the sample pad to the conjugate pad (or from the sample area to the conjugate area), and then the liquid advances through the conjugate pad (or area), and then through the chromatographic membrane. As the liquid advances through the apparatus, the conjugate pad (where the anti-analyte antibody-particle conjugate is located) is exposed to the liquid, and the anti-analyte antibody-particle conjugate becomes at least partially dissolved in the liquid.

In some embodiments, aptamers may be used instead of or in addition to antibodies. For ease of discussion the term antibodies is used throughout this application, but throughout the specification should be understood to encompass both antibodies and aptamers.

The method further includes determining whether an interaction between the anti-drug antibody-particle conjugate and the liquid occurs to detect the presence of the analyte. The determining step comprises monitoring the test line (where the analyte-conjugate protein is located) to observe whether the test line develops color, and optionally whether a control line develops color, as described below. Thus, the determining step comprises observing a visual indication to determine presence or absence of the analyte.

If the liquid contains an analyte that matches the anti-analyte antibody of the anti-analyte antibody-particle conjugate, the analyte will bind to the anti-analyte antibody portion of the conjugate, and because the anti-analyte portion of the conjugate is bound to the analyte, the anti-analyte antibody portion cannot not bind to the analyte-conjugate protein, and no color will be deposited at the test line. However, if the liquid is substantially free from an analyte that matches the anti-analyte antibody of the anti-analyte antibody-particle conjugate, the anti-analyte antibody-particle conjugate will bind to the analyte-conjugate protein and color will be deposited at the test line.

Optionally, the chromatographic membrane may comprise an anti-species antibody at a control line. Regardless of whether an analyte is bound to the anti-analyte antibody-particle conjugate, the control line will develop color when the anti-analyte antibody-particle conjugate is drawn by the liquid to the control line.

Using a competitive (indirect) immunoassay format, a result indicating that no analyte is present consists of two lines (test and control lines are visible) while a result indicating that analyte is present consists of one line (control line is visible) in some examples. In other examples where a control line is not employed, a result indicating that no analyte is present consists of one line (test line is visible) while a result indicating that analyte is present consists of no line. Areas of color deposition are not limited to lines, and may comprise symbols or patterns. The phrases "test line, test location, test pattern, test symbol, and test area" may be used interchangeably. The phrases "control line, control location, control pattern, control symbol, and control area" may be used interchangeably. Alternately, a direct immunoassay format may be used, where the visible presence of a test line indicates the target analyte is present.

In some embodiments, the method comprises observing a visual indication or signal mechanism as to whether a particular compound is present. For example, the indication can comprise the appearance of a colored dot, pattern, or region, the absence of any appearance of a colored region, the printing of words, such as "SAFE," "OK," "YES," or "NO," checkmarks, emoticons or symbols such as a "☺," fluorescence, vibration, or sounds. In some examples, the signaling mechanism comprises completing lines, logos, patterns or symbols. In some embodiments, if the pattern has been created to detect multiple analytes, only a certain portion of the pattern may change color. For example, the word "SAFE" may appear as SAFE, where the color of the letter "A" has not developed in the cross-bar region.

The method described herein does not rely on the observation or measurement of color change of the anti-analyte antibody-particle conjugate to detect the presence of an analyte in a liquid. The method described herein does not rely on other techniques, such as electrophoresis. The method relies on observing color deposition (or lack thereof) at the test and/or control lines, area, or patterns, or regions.

Any of the apparatus described in the section below may be used in the methods described herein.

III. Apparatus

Certain embodiments described herein provide an apparatus for detecting the presence of a targeted substance, analyte, or drug in a liquid, wherein the apparatus comprises a sample pad, a conjugate pad, and a detection layer, and in some cases, a wick. In some embodiments, the detection layer can detect the presence of a particular substance upon receiving a liquid to be tested for the particular targeted substance. For example, the sample pad can be exposed to the liquid in question and then the apparatus may be monitored by a user to determine whether there is a particular interaction between the detection layer and the liquid to indicate the presence of the targeted substance. In some embodiments, the particular substance is a benzodiazepine or an amine-containing compound. In other embodiments, the particular substance is a protein or sugar.

In other examples, the apparatus comprises a single pad comprising separate areas, such as a sample area, a conjugate area, a detection layer (or chromatographic membrane area), and a wick area. In still other examples, the apparatus comprises a single pad comprising separate areas, such as a sample area, a conjugate area, and a detection layer (or chromatographic membrane area).

In some embodiments, the apparatus can be configured to minimize, substantially reduce, or eliminate backflow. This backflow or potential flow of components from the apparatus to the test liquid may be undesirable, especially for testing of consumable liquids. In some embodiments, the potential backflow/reverse flow may comprise the test liquid and chemicals from the apparatus. To address the potential for backflow, in some embodiments, the detection layer may further comprise an untreated pad at the sample port or opening in the top layer to substantially eliminate backflow. The untreated pad may minimize, substantially reduce, or eliminate potential flow of material back to the test liquid due to saturation of the untreated pad upon introduction of the apparatus into the test liquid. Once introduced into the test liquid, the saturated untreated pad may serve as a constraint on backflow by minimizing the gradient and motive force of flow from the sample pad to the test liquid. This constraint of the saturated untreated pad may help ensure that essentially none of the chemical additives or buffers from the apparatus come in contact with the test liquid. In some examples, preventing backflow can be achieved by using an untreated sample pad and/or by designing the apparatus to encase the components of apparatus (other than the untreated pad and/or sample pad) in a plastic housing.

In some embodiments, the apparatus is a lateral flow device for a lateral flow assay, whereby a liquid to be analyzed migrates along a fluid path from a sample area, across a conjugate area, across a chromatographic membrane, and into a wick. The target substance or analyte, if present, reacts with an anti-analyte antibody and the reaction results in a visual indication of whether the target analyte is present in the liquid. In some examples, aptamers may be used instead of or in addition to antibodies. Lateral flow assays typically have a fluid path along the length of the apparatus. In some examples disclosed herein the length of the fluid path is the same as the length of the apparatus. In other examples, the length of the fluid path is greater than the length of the apparatus, Although the term "lateral flow" is used throughout this specification, in some cases the fluid path may vary in the x-y plane or in the z direction in order to achieve detection results in an apparatus with a confined length. In such embodiments, the length of the fluid path typically is greater than the length of the apparatus.

An apparatus for detecting the presence of a targeted substance in a liquid comprises a sample pad; a conjugate pad that includes a binder-particle conjugate, such as an anti-analyte antibody-particle conjugate; and a chromatographic membrane, optionally including an analyte-conjugate protein. In some embodiments, the sample pad and the conjugate pad are formed from a single material comprising a sample area and a conjugate area; the sample area and the conjugate area do not overlap. In some embodiments, the anti-analyte antibody-particle conjugate can be included in the conjugate pad by depositing a composition comprising an anti-analyte antibody-particle conjugate on the chromatographic membrane from a conjugate dilution buffer. The analyte-conjugate protein can be included in the chromatographic membrane at a test location by depositing a composition comprising an analyte-conjugate protein on the chromatographic membrane in a line or desired pattern. Optionally, an anti-species antibody can be included in the chromatographic membrane at a control location by contacting the chromatographic membrane with a composition comprising an anti-species antibody.

The wick serves a fluid reservoir to keep fluid moving through the chromatographic membrane. In some embodiments, in order to miniaturize the assay, the wick is comprised of a folded layer (e.g., the layer is folded back upon itself). In some embodiments, the wick is U-shaped or S-shaped. In some cases, the fluid path in the wick may be curved through multiple planes and/or in multiple directions according to the shape of the wick. As the fluid flows from the chromatographic membrane to the wick, it continues along a fluid path within the wick. In some examples, the fluid path through the wick is not aligned with the path of the fluid through the chromatographic membrane, as the wick may direct the fluid path to the sides of and/or around or under the chromatographic membrane.

In some embodiments, the apparatus can be configured to direct flow of a liquid through the detection layer (or chromatographic membrane) in a generally horizontal orientation, e.g., substantially along a single horizontal plane from a first end of the detection layer to the second end of the detection layer. In other embodiments, the detection layer can be configured to direct flow of a liquid through the detection layer in a generally vertical orientation, e.g., substantially through a plurality of horizontal planes, for example, from the bottom of the detecting layer to the top of the detecting layer, resulting in the length of the fluid path being greater than the length of the apparatus.

In some examples, as a result of the length of the fluid path being greater than the length of the apparatus, the length of the apparatus may be shortened without impeding the detection ability of the apparatus. In some cases, the length of the fluid path is from 5-10% greater than the length of the apparatus, from 10-20% greater than the length of the apparatus, from 20-30% greater than the length of the apparatus, from 30-40% greater than the length of the apparatus, from 50-75% greater than the length of the apparatus, from 75-100% greater than the length of the apparatus, or from 100-200% greater than the length of the apparatus.

The apparatus can be positioned on the surface of an object. In some examples, the apparatus can be positioned on, integrated in, or incorporated in an object. In other examples, the apparatus can be positioned below, or below the surface of, an object. Suitable objects include, for example, a natural fingernail, an artificial fingernail, a layer of fingernail polish, a fingernail sticker, a fingernail decal, a cup, a drink coaster, a drink stirrer, a toothpick, a drink ornament (e.g., an umbrella), a pencil, a pen, a test strip, a sticker, a decal, a nail decal, a mesh nail wrap, or any other appropriate surface or structure. In other embodiments, the apparatus may be positioned directly on skin, such as on a finger.

In some embodiments, the apparatus comprises a thickness ranging from about 0.2 micrometers (μm) to about 5 millimeters (mm). In some embodiments, the apparatus comprises a thickness ranging from about 20 μm to about 5 mm. In some embodiments, the detection layer can have a thickness of about 0.6 μm or less, 1 μm or less, 10 μm or less, 25 μm or less, 50 μm or less, 100 μm or less, 1 mm or less, 2 mm or less, 3 mm or less, 4 mm or less, or 5 mm or less.

In some embodiments, the apparatus comprises a length ranging from about 0.5 mm to about 15 mm. In some embodiments, the apparatus comprises a length ranging from about 1 mm to about 10 mm, or from about 3 to about 8 mm. In some embodiments, the detection layer can have a length of about 0.4 mm or less, 0.5 or less, 1 mm or less, 2 mm or less, 3 mm or less, 4 mm or less, 5 mm or less, 6 mm or less, 7 mm or less, 8 mm or less, 9 mm or less, 10 mm or less, 12 mm or less, or 15 mm or less.

In some embodiments, the apparatus comprises a width ranging from about 0.5 mm to about 5 mm. In some embodiments, the apparatus comprises a width ranging from about 1 mm to about 10 mm, or from about 3 to about 8 mm. In some embodiments, the detection layer can have a width of about 0.4 mm or less, 0.5 or less, 1 mm or less, 2 mm or less, 3 mm or less, 4 mm or less, 5 mm or less, 6 mm or less, 7 mm or less, 8 mm or less, 9 mm or less, or 10 mm or less.

In some embodiments, the apparatus can be laminated to provide protection from the external environment without compromising the integrity of the test by permitting gas permeability during use.

Turning now to the Figures, FIG. 1 is an exploded cross-section view of an apparatus 100 according to one embodiment described herein. Apparatus 100 comprises a sample pad 110, a conjugate pad 120, a detection layer 130 and an absorption pad or wick 160. The sample pad 110 is adjacent to a first portion 122 of the conjugate pad 120 so that in use a liquid is absorbed into the conjugate pad 120 from the sample pad 110. A second portion 124 of the conjugate pad is adjacent to the chromatographic membrane 130 at a proximal end 132 of the chromatographic membrane 130 so that in use a liquid is absorbed into the chromatographic membrane at the proximal end 132 and moves through the chromatographic membrane toward the distal end 134 of the chromatographic membrane 130. Between the proximal and distal ends the chromatographic membrane includes at least one test line 140 where an analyte-conjugated protein is deposited and at least one control line 150 where an anti-species antibody is deposited. The apparatus also comprises an absorption pad or wick 160 adjacent to the chromatographic membrane 130 so that in use liquid is absorbed into the wick from the chromatographic membrane 130. In some embodiments multiple test lines may be present to test for a plurality of targeted substances. Optionally, the apparatus may have a clear cover layer 170.

Figure 2:
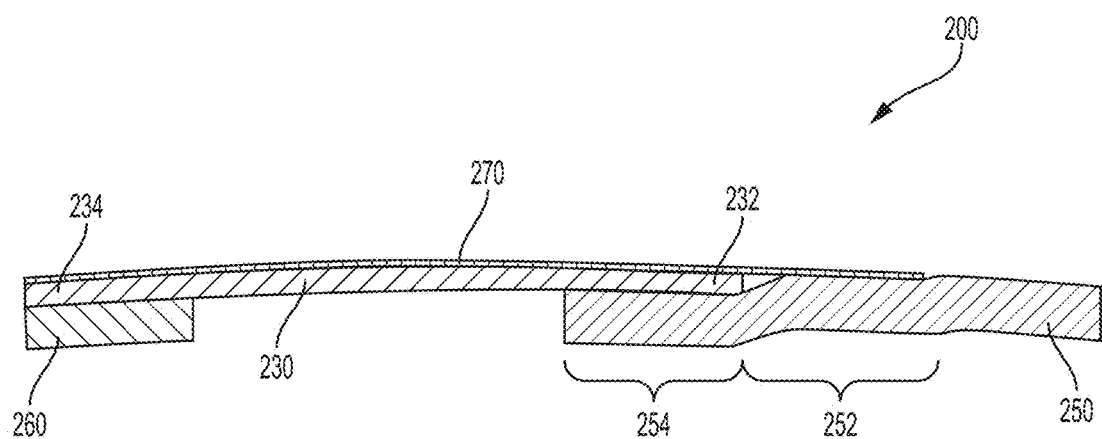
FIG. 2 is a cross-sectional view of an apparatus according to some embodiments described herein.

FIG. 2 is a cross-section view of an apparatus 200 according to one embodiment described herein. Apparatus 200 comprises a combined sample pad-conjugate pad 250 which has a sample area 252 and a conjugate area 254 that do not overlap. Apparatus 200 further comprises a detection layer 230 and a wick 260. The conjugate area 254 of the sample-conjugate pad 250 is adjacent to a first portion 232 of the detection layer 230 so that in use a liquid is absorbed into the sample-conjugate pad 250, migrates into a proximal end 232 of the chromatographic membrane 230, and flows toward the distal end 234 of the chromatographic membrane 230. The apparatus also comprises an absorption pad or wick 260 adjacent to the distal end 234 chromatographic membrane 230 so that in use a test liquid is absorbed into the wick from the chromatographic membrane 230. Optionally, the apparatus may have a clear cover layer 270.

In some embodiments, the sample pad is pretreated with a sample pad buffer solution. Pretreatment involves contacting the sample pad with the sample pad buffer solution and then drying the sample pad. The dried sample pad comprises a residual buffer composition. In use, when a test liquid contacts the residual buffer composition, the buffer is reconstituted in the test liquid. In some embodiments, the sample pad may be pretreated with a sample pad buffer solution consisting essentially of biocompatible materials so that any potential interaction of the sample pad buffer ingredients with a beverage will not introduce material unsuitable for ingestion into the beverage. In some embodiments, the sample pad buffer aids in neutralization of the acidic beverages, and may also reduce the impact of other components, such as high sugar content, on test results. For purposes of this application, "sample pad buffer solution" and "sample area buffer solution" may be used interchangeably.

In some embodiments, the sample pad buffer solution comprises potassium carbonate and/or calcium carbonate. In some embodiments, the sample pad buffer solution comprises a calcium salt of a weak acid.

In some embodiments the sample pad buffer solution comprises potassium carbonate. In some embodiments, potassium carbonate is present in the sample pad buffer solution in a concentration of from 200 to 3000 millimolar (mM), from 500 to 2000 mM, from 750 to 1500 mM, from 0.8 to 1.2 molar (M), from 0.9 to 1.1 M, or about 1 M. In some embodiments, potassium carbonate is present in the sample pad buffer solution in a concentration of at least 800 mM, at least 900 mM, at least 1.0 M, at least 1.1 M, at least 1.2 M, or at least 1.3 M. Optionally, in some embodiments, the sample pad buffer solution may comprise hydroxide, borate, and/or bicarbonate salts.

In some examples, the conjugate pad may be pretreated with conjugate pad buffer solution comprising a stabilizing agent and/or a shielding agent. Examples of stabilizing agents include saccharides such as sucrose, fructose, and trehalose. Examples of shielding agents include gelatin, casein, and BSA.

In some examples, the conjugate pad buffer solution comprises a buffer salt.

Tris(hydroxymethyl) aminomethane (Tris) was found to be particularly effective at neutralizing, and therefore mitigating negative effects, of acidic beverages on test results. In some embodiments, the conjugate pad buffer solution has a pH from 7.5 to 8.5, from 7.75 to 8.25, from 7.9 to 8.1, or about 7.8, about 8.0, or about 8.2. Other buffer solutions, such as sodium borate buffer solutions, in some examples could not be prepared in concentrations high enough to provide the necessary buffering capacity for the conjugate pad. An usually high concentration of buffer solution is required due to the a very limited area (such as a 4×4 mm conjugate pad) to be impregnated with the conjugate pad buffer solution, which is dried, and then is reconstituted as the sample liquid flows through the conjugate pad. In some embodiments, the conjugate pad buffer solution comprises Tris in a concentration of from 0.4 to 0.6 molar (M), from 0.423 to 0.575 M, from 0.45 to 0.55 M. In some embodiments, the conjugate pad buffer solution comprises Tris in a concentration of about 0.4 M, about 0.5 M, or about 0.6 M.

In some embodiments, the conjugate pad buffer solution further comprises one or more of a protein, a poly(vinylpyrrolidone), and a surfactant. Some non-limiting examples of surfactants are Aerosol OT, benzalkonium chloride, BRIJ35, BRIJ 52, BRIJ98, CHEMAL-LA-9, Cremophore EL, IGEPAL CA210, Merpol A, Pluronic F68, Pluronic F127, Pluronic L64, Silwet L7600, Surfactant 10G, Synperonic F108, 2,4,7,9,-tetramethyl-5-decyn-4,7-diol ethoxylate, Tergitol, Tetronic 90R4, Triton X-45, Triton X 100, Triton X-305, Tween-20, Tween-60, and Tween-80. In some embodiments, the protein is BSA and the poly(vinylpyrrolidone) is PVP-40. In some embodiments, the surfactant comprises Triton X-100, Triton X-305 and/or Pluronic F68. In some examples, BRIJ-98 was found to reduce background coloration caused by beverages. Not intending to be bound by theory, BRIJ-98 causes precipitation of many colored red wine components. In some embodiments, the residual buffer composition can substantially reduce or substantially remove the appearance of colored components of a test liquid. "Substantially reduce or substantially reduce" means that the color of the test liquid does not interfere with the indication of test results.

In some embodiments, the conjugate pad buffer composition is compatible with the anti-analyte antibody-particle conjugate, for example, the conjugate pad buffer composition, when reconstituted by the test liquid, does not denature the anti-analyte antibody-particle conjugate. Not intending to be bound by theory, this may be due to the high pH of the conjugate pad buffer and the resulting neutralization of acid in test liquids such as beverages.

The conjugate is not bound to the conjugate pad; rather, it is adhered or immobilized, so that the conjugate is released to the test liquid and flows with the test liquid across the chromatographic membrane. In some embodiments of the invention, the conjugate pad and the sample pad are formed from a single piece of material, such as nitrocellulose or a woven mesh of glass fibers or polyester fibers.

In some embodiments, the anti-analyte antibody-particle conjugate may be prepared from a commercially available monoclonal antibody and a gold or dye nanoparticle material. In some embodiments, the commercially available monoclonal antibody may be desalted using a spin column to replace the antibody storage buffer with an antibody desalting buffer. In some embodiments, the antibody desalting buffer comprises a sodium phosphate buffer. A sodium phosphate antibody desalting buffer may have a concentration of 5 mM, 10 mM, 25 mM, 50 mM, 75 mM, 100 mM, 125 mM, or 150 mM, or from 50-150 mM, or from 75-125 mM, or from 90-110 mM. In some embodiments, the antibody desalting buffer may have a slightly basic pH, such as 7.2, 7.3, 7.4, 7.5, 7.6, 7.7, 7.8, 7.9, 8.0, 8.1, or 8.2. When the antibody has been desalted and is dissolved in the antibody desalting buffer, it may be conjugated with a gold or dye nanoparticle material. In some embodiments, the gold or dye nanoparticle material may be dissolved or suspended in water with the pH adjusted to slightly basic, such as pH 7.05, 7.1, 7.15, 7.2 or 7.25 by the addition of HCl or NaOH.

In some embodiments, after the antibody is dissolved in the antibody desalting buffer and the gold or dye nanoparticle is dissolved or suspended in slightly basic water, the two components are mixed, and a conjugation blocking buffer may be added to the resulting mixture. In some embodiments, the conjugation blocking buffer comprises sodium tetraborate, boric acid, and BSA. In some embodiments, the blocking buffer can have a sodium tetraborate concentration of 10 mM, 25 mM, 50 mM, 75 mM, or 100 mM, or from 10-110 mM, or from 25-75 mM, or from 45-55 mM. In some embodiments, the conjugation blocking buffer may have a basic pH, such as 8.2, 8.4, 8.6, 8.8, 9.0, 9.2, 9.4, or 9.6. The resulting anti-analyte antibody-particle conjugate may be isolated as a pellet by centrifugation.

In some embodiments, the anti-analyte antibody-particle conjugate is applied to the conjugate pad from a conjugate dilution buffer which may be used to reconstitute the anti-analyte antibody-particle conjugate pellet. In some embodiments, the anti-analyte antibody-particle conjugate is dissolved in a conjugate dilution buffer prior to depositing the anti-analyte antibody-particle conjugate on the conjugate pad.

In some embodiments, the conjugate dilution buffer comprises a salt of a weak acid, a protein, and optionally, excipients such as saccharides. In some embodiments, the conjugate dilution buffer comprises a borate, such as sodium tetraborate, boric acid, BSA, and optionally, sucrose and/or trehalose. In some examples, the conjugate dilution buffer comprises 40-60 mM, 45-55 mM or about 50 mM borate, 1-3 weight percent (wt. %) BSA (e.g. 1 wt. %, 2 wt %, or 3 wt. %), 3-7 wt. % trehalose (e.g. 4 wt. %, 5 wt %, or 6 wt. %), and 15-25 wt. % sucrose (e.g. 18 wt. %, 20 wt %, or 22 wt. %). In some embodiments the conjugate dilution buffer has a pH of from 8.5 to 9.5, (e.g. 8.7, 9.0, or 9.3). In some embodiments, the pH of the conjugate dilution buffer is titrated.

In some examples, the conjugate dilution buffer comprises 40-60 mM, 45-55 mM or about 50 mM borate, 1-3 weight percent (wt. %) BSA (e.g. 1 wt. %, 2 wt %, or 3 wt. %), and sucrose and/or trehalose are added after the conjugate has been dissolved in the conjugate dilution buffer. In some embodiments, sucrose is added in an amount of 10%, 20%, or 30%, where 20% is determined, for example, according to the formula (volume of conjugate in conjugate dilution buffer)(20 g sucrose)/(100 mL). Similarly, in some embodiments, trehalose is added in an amount of 3%, 5%, or 7%, where 5% is determined, for example, according to the formula (volume of conjugate in conjugate dilution buffer)(5 g trehalose)/(100 mL).

In some embodiments, any of the buffer solutions or buffer additives described herein has a viscosity of at least 10 cP. In other embodiments, the buffer or buffer additives can comprise a viscosity of at least 0.5 cP, at least 1 cP, at least 5 cP, at least 20 cP, at least 30 cP, at least 60 cP, at least 80 cP, at least 100 cP, at least 1000 cP, at least 20,000 cP, or at least 50,000 cP. In other embodiments, the buffer or buffer additives can comprise a viscosity of between 0.5-2 cP, between 2-5 cP, between 5-20 cP, between 20-30 cP, between 30-60 cP, between 1-100 cP, between 2-80 cP, between 5-50 cP, between 10-1000 cP, between 10-20,000 cP, or between 10-50,000 cP. In some embodiments, the chromatographic membrane may be pretreated with a chromatographic membrane buffer solution comprising 10-20 mM or 12-18 mM or about 15 mM sodium phosphate, 0.5-1.5 wt. % or 0.7 to 1.3 wt. %, or about 1 wt. % sucrose, 0.05-0.15 wt. % or 0.7 to 1.2 wt. % or about 1 wt. % BSA, and 0.1-0.3 wt. % or about 0.2 wt. % PVP-40. In some embodiments, the chromatographic membrane buffer has a pH from 7.1 to 7.5. In some embodiments, the chromatographic membrane buffer may have a pH of 7.1, 7.2, 7.3, 7.4, or 7.5, or from 7.1-7.5, or from 7.2 to 7.4, or from 7.25-7.35.

The detection layer of certain embodiments described herein can provide an visual indication or signal mechanism to a user as to whether a particular compound is present. For example, the visual indication can comprise the appearance, or lack thereof, of a colored dot, pattern, or region; the printing of words, such as "SAFE," "OK," "YES," or "NO"; checkmarks, emoticons or symbols such as a "☺," fluorescence, vibration, or sounds.

In some embodiments, the detection layer can provide an indication to a user by electrochemical detection. In some examples the detection layer can provide a device-aided quantitation, for example with the aid of smartphone application or other device. In some embodiments, the detection layer can provide a semi-quantitative or quantitative indication of the analyte in the liquid. In some examples, the indication of the analyte present in the liquid comprises a pattern of lines. For example, in one embodiment, 6 test lines may be placed on the detection layer. When a direct immunoassay format is used, if the analyte is present in certain quantities, one test line may develop color. If the analyte is present in certain, larger quantities, additional test lines may develop color. If the analyte is present in an even greater amount, all test lines may develop color.

Alternately, when an indirect immunoassay format is used, if the analyte is present in certain quantities, one test line may develop color. If the analyte is present in certain, lesser quantities, additional test lines may develop color. If the analyte is present in an even lesser amount, all test lines may develop color. In some examples, during the assembly of the apparatus, the test line is deposited from a buffer solution in a low-to-high concentration gradient in the direction of liquid flow across the chromatographic membrane to create a 2 mm test line with no leading edge effect. "Leading edge effect" refers to the formation of a color gradient at the test or control lines where the darkest area is along the leading edge of the line and the color of the line become progressively lighter as it nears the distal edge. The "leading edge" of the test/control line is the side of the line which contacts the fluid first as it flows through the membrane.

In some embodiments, the detection layer comprises a thickness ranging from about 50 microns to about 1000 microns. In some embodiments, the detection layer comprises a thickness ranging from about 200 microns to about 400 microns. In some embodiments, the detection layer can have a thickness of about 100 microns or less, 200 microns or less, 400 microns or less, 600 microns or less, 800 microns or less, or 1000 microns or less.

In some embodiments, the detection layer can be configured to detect the presence of a plurality of targeted substances. In some embodiments, the detection layer can be physically divided to permit the detecting of multiple analytes without inferring with the detection of another analyte. As another example, a detection layer can be multiplexed with certain components to test for multiple analytes on a single detection layer. In some embodiments, the apparatus can include a plurality of discrete, physical sections positioned adjacent to each other to make up a single detection layer. For example, a plurality of matrices can be positioned side by side with each matrix configured to test for the presence of a different compound in a liquid.

In some embodiments, the apparatus comprising a detection layer can also include at least one additional layer. In some embodiments, the apparatus can include at least one of a top laminate layer, a bottom laminate layer, and a removable layer. In some embodiments, the apparatus can include any combination of layers described herein.

In some examples, an apparatus described herein includes a specific combination of residual buffer formulations that can render the apparatus compatible with a wide range of test fluids. For example, a first residual buffer formulation may be used at a location near the beginning of the liquid flow path, for example the sample area, to interact with components in the test fluid that could be detrimental to test results, such as acids, alcohol, and/or colorants, and a second residual buffer formulation may be used at a separate location further down the liquid flow path to buffer the test liquid near a certain pH so as not to denature proteins involved in the assay.

In addition, a specific combination of buffer formulations can allow combining multiple detection means (such as using two or more marker-test line combinations) for detecting multiple analytes, whereas in the absence of the specific combination of residual buffer formulations the different detection means would not be compatible with the same scope of test fluids. In one example, in the absence of a particular residual buffer formulation, a first detection means for detecting a first analyte is only compatible with test fluids A and B, and a second detection means for detecting a second analyte is only compatible with test fluids B and C. In that case, the first and second means could not be used in combination to simultaneously detect the first and second analytes in fluids A and C. But a single apparatus including an appropriate combination of residual buffer formulations is compatible with fluids A, B, and C, and can detect the first and the second analytes in all three fluids. This "multiplexing" is useful for the detection of multiple analytes with may require different detection means (such as different antibodies, aptamers, or markers) with a single apparatus. In some examples, an apparatus described herein may detect the presence of both benzodiazepines and ketamines.

Anti-analyte Antibody-particle Conjugates

In some embodiments, the anti-analyte antibody-particle conjugate described herein includes an anti-analyte antibody, a colored nanoparticle, and optionally one or more additional components.

An antibody is a large, Y-shaped protein produced mainly by plasma cells that is used by the immune system to identify and bind pathogens such as bacteria and viruses. Aptamers are oligonucleotide or peptide molecules that bind to a specific target molecule. The anti-analyte antibody or anti-analyte aptamer is an antibody or aptamer that is formed to bind a specific analyte such as a drug molecule. As understood by a person of ordinary skill in the art, immunoassay techniques employ this "lock and key" approach, using a specific antibody or aptamer to bind with a targeted substance.

Particles to enhance visibility and/or detection are frequently attached to the anti-analyte antibody to increase visibility and/or detection of the anti-analyte antibody. Useful particles may comprise colored compounds or fluorescent compounds. In some embodiments, the particle comprises fluorescein, Rose Bengal, derivatives and salts thereof, or combinations thereof, or similar fluorophores. In other embodiments, nanoparticles are used as particles. The nanoparticle may be any colored nanoparticle such as gold and/or dye-infused polymer microbeads.

The anti-analyte antibody is joined, or conjugated, to the particle by a linker. The linker may be any linker that is not inconsistent with the objectives of the current invention. Non-limiting examples of linkers are (N-(κ-maleimidoundecanoyloxy) sulfosuccinimide ester) (sulfo-KMUS), (succinimidyl-4-(N-maleimidomethyl)cyclohexane-1-carboxy-(6-amidocaproate)) (LC-SMCC), N-(e-maleimidcCaproyloxy)-N-HydroxySuccinimide ester (KMUs), succinimidyl-4-(p-maleimidophenyl)butyrate (SMBP), (succinimidyl-6-((b-maleimidopropionamido) hexanoate) (SMPH), 4-(N-maleimidomethyl)cyclohexanecarboxylic acid N-hydroxysuccinimide ester (SMCC), 4-(N-maleimidomethyl)cyclohexane-1-carboxylic acid 3-sulfo-N-hydroxysuccinimide ester sodium salt (sulfo-SMCC), (N-succinimidyl (4-iodoacetyl)aminobenzoate) (SIAB), N-(γ-maleimidobutyryloxy)sulfosuccinimide sodium salt (sulfo-GMBS), 4-maleimidobutyric acid N-hydroxysuccinimide ester (GMBS), (succinimidyl 3-(bromoacetamido)propionate) (SBAP), N-(2-carboxyethyl)maleimide (BMPA), N-α-maleimidoacet-oxysuccinimide ester (AMAS), N-succinimidyl 3-(acetylthio)propionate (SATP), 3-maleimidobenzoic acid N-hydroxysuccinimide ester (MBS), (m-maleimidobenzoyl-N-hydroxysulfosuccinimide ester) (sulfo-MBS), N-ε-maleimidocaproic acid (EMCA), N-(ε-maleimidocaproyloxy)succinimide, N-succinimidyl 6-maleimidocaproate (EMCS), succinimidyl-(4-vinyl sulfone)benzoate (SVSB), N-succinimidyl 3-maleimidopropionate (BMPS), or N-ethyl-N'-(3-dimethylaminopropyl)carbodiimide hydrochloride (EDC). In some embodiments, the gold nanoparticles are functionalized with compounds such as 6-mercaptohexanoic acid, 8-mercaptooctanoic acid, 12-mercaptododecanoic acids, or other mercapto-carboxylic acids. Reagents such as EDC may be used to couple the antibodies to these reagents. Polymer microbeads may be functionalized with similar carboxylic acids or amines.

The anti-analyte antibody-particle conjugate can be present in an anti-analyte antibody-particle conjugate composition in an amount of from about 0.05 wt. % to about 10 wt. % (e.g., from about 0.5 wt. % to about 8 wt. % or from about 0.8 wt. % to about 5 wt. %). For example, the anti-analyte antibody-particle conjugate can be present in the anti-analyte antibody-particle conjugate composition in an amount of about 10 wt. % or less, about 9.5 wt. % or less, about 9 wt. % or less, about 8.5 wt. % or less, about 8 wt. % or less, about 7.5 wt. % or less, about 7 wt. % or less, about 6.5 wt. % or less, about 6 wt. % or less, about 5.5 wt. % or less, about 5 wt. % or less, about 4.5 wt. % or less, about 4 wt. %, about 3.5 wt. % or less, about 3 wt. % or less, about 2.5 wt. % or less, about 2 wt. % or less, about 1.5 wt. % or less, about 1 wt. % or less, or about 0.5 wt. % or less. In some embodiments, the anti-analyte antibody-particle conjugate can be present in the anti-analyte antibody-particle conjugate composition in an amount of about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1 wt. %, about 1.5 wt. %, about 2 wt. %, about 2.5 wt. %, about 3 wt. %, about 3.5 wt. %, about 4 wt. %, about 4.5 wt. %, or about 5 wt. %.

A buffering agent can be present in the conjugate dilution buffer such that pH of the total marker composition is from about 5 to about 9 (e.g., from about 6 to about 8 or from about 6.5 to about 7.5). For example, the buffering agent can be added to the composition to provide a pH of about 5, about 5.5, about 6, about 6.5, about 7, about 7.5, or about 8.

The composition can further include a solvent carrier. A suitable solvent carrier includes water (e.g., deionized water). Optionally, the solvent carrier can further include one or more organic solvents, such as alcohols, glycols, and other liquids.

Analyte-conjugate Protein

The analyte-conjugate protein comprises the analyte that is to be detected conjugated or linked to a protein. Examples of suitable proteins are BSA, CRM197, KLH, thyroglobulin, tetanus toxoid, rabbit serum albumin, myoglobulins, tuberculin, poly-lysine, and/or poly-glutamic acid.

Anti-species Antibody

The anti-species antibody is capable of binding with the anti-analyte antibody-particle conjugate. Because the anti-species antibody will bind with the anti-analyte antibody-particle conjugate whether or not an analyte is present in the liquid, the location where the anti-species antibody has been deposited will develop color when the liquid contains an anti-analyte antibody-particle conjugate.

Chromatographic Membrane

As described above, the detection layer comprises a chromatographic membrane. In some embodiments, the chromatographic membrane comprises, may consist essentially of, or may be formed from cellulose or cellulose derivatives, including surface-functionalized cellulose, glass fiber, and/or other materials. In some embodiments, the chromatographic membrane comprises a porous chromatography medium. Typical pore size may comprise a diameter of about 10 to 14 μm, although other size pores may be used. The chromatography medium may be hydrophobic or hydrophilic, and may comprise inorganic powders such as silica, magnesium sulfate, and alumina; natural polymeric materials, particularly cellulosic materials and materials derived from cellulose, such as fiber containing papers, for example, filter paper or chromatographic paper.; synthetic or modified naturally occurring polymers, such as nitrocellulose, cellulose acetate; poly(vinyl chloride), polyacrylamide, agarose, or polyacrylate; alone or in combination with other materials. Ceramics may also be used. Optionally, the chromatography medium can be bound to a backing layer.

Optionally, the chromatographic membrane may comprise one or more polymers. Optionally, the one or more polymers includes polysaccharides. Suitable polysaccharides for use in the chromatographic membrane include agar, agarose, alginate, carrageenan, cellulose, chitosan, dextran, konjac, and mixtures thereof. Exemplary agarose polymers include, for example, carboxymethyl agarose, diethylaminoethyl agarose, and like derivatives. Optionally, the agarose polymers for use in the chromatographic membrane are commercially available from Pharmacia Fine Chemicals, Inc. (Piscataway, N.J.). Exemplary cellulose polymers include, for example, cellulose esters (e.g., cellulose acetate, cellulose acetate butyrate, cellulose acetate propionate), carboxymethyl cellulose, diethylaminoethyl (DEAE) cellulose, nitrocellulose, phosphocellulose, quaternary ammonium substituted cellulose, and sulfoxyethyl cellulose. Optionally, the cellulose polymers for use in the matrix are commercially available from Whatman Co. (Whatman Paper Co., Ltd., Maidstone, England) or BioRad Corp. (Richmond, Calif.). In some embodiments, the chromatographic membrane includes glass fiber. Glass and polyester fiber may be acquired from Fusion 5 from GE Healthcare (GE Healthcare, Little Chalfont, UK).

The chromatographic membrane can further include an absorbent. For example, the absorbent can include chromatography paper, filter paper, and other materials typically used for chromatography, such as for paper chromatography or thin layer chromatography (TLC). The chromatography paper and filter paper can be qualitative or quantitative filter paper, such as the chromatography paper and filter paper commercially available from Whatman Co. (Whatman Paper Co., Ltd., Maidstone, England).

Optionally, the absorbent comprises silica gel, alumina, high performance thin layer chromatography (HPTLC) silica gel, polysilicic acid, aluminum oxide, cellulose, polyamide, reversed phase silica gel $C_2$ (dimethyl bonded), reversed phase silica gel $C_2$ (ethyl bonded), reversed phase silica gel $C_8$ (octyl bonded), reversed phase silica gel $C_{18}$ (octadecyl bonded), acetylated cellulose, silica gel modified with amino groups, silica gel modified with cyano groups, Kieselghur impregnated with hydrocarbons, anionic and cationic anion exchange resins, diethylaminoethyl cellulose, and mixtures of the listed sorbents. The absorbent can be immobilized on an inert surface.

Optionally, the chromatographic membrane can be pre-treated with a desiccant to integrate the desiccant into the chromatographic membrane. The desiccant can be any desiccant as known to those of skill in the art, including, but not limited to, molecular sieves, silica gels, clays, synthetic polymers, and starches. For example, suitable desiccants include alumina, bauxite, anhydrous calcium sulfate, water-absorbing clays, silica gel, zeolite, and mixtures thereof.

Optionally, the chromatographic membrane can be pre-treated with a buffering agent, such as the buffering agents described above. The matrix can be pre-treated with a buffering agent such that the matrix is buffered at a pH ranging from about 3 to about 8 (e.g., from about 4 to about 6 or from about 4.5 to about 5.5). For example, the buffering agent can be added to the composition to provide a pH of about 3, about 3.5, about 4, about 4.5, about 5, about 5.5, about 6, about 6.5, about 7, about 7.5, or about 8.

The chromatographic membrane can be positioned on the surface of an object. In some examples, the matrix can be positioned within an object. In other examples, the chromatographic membrane can be positioned below the surface of an object. Suitable objects include, for example, a fingernail, an artificial fingernail, a layer of fingernail polish, a fingernail sticker, a fingernail decal, a cup, a bar coaster, a drink stirrer, a toothpick, a drink ornament (e.g., an umbrella), a pencil, a pen, a test strip, a sticker, a decal, a nail decal, a mesh nail wrap, or any other appropriate surface. Other appropriate surfaces include items that could easily and discreetly be brought into contact with a suspect liquid, providing an improved degree of personal security for the liquid consumer.

The apparatus described herein can also include a cover over the chromatographic membrane. The cover can be an opaque cover, a tinted cover, a transparent cover, or a translucent cover. Optionally, the cover can include one or more perforations. These perforations allow for the escape of gaseous materials during the use of the apparatus. In examples where the cover is opaque, tinted, or translucent, the cover can optionally include one or more transparent windows on the cover. The cover can be attached to the apparatus using any suitable binding material as known to those of skill in the art, including, for example, an adhesive. Suitable adhesives include but are not limited to acrylic and methacrylic ester homo- or copolymers, butyl rubber based systems, silicones, urethanes, vinyl esters and amides, olefin copolymer materials, di-alkyl fumarates, natural or synthetic rubbers, and the like, including hot-melt adhesives.

In some embodiments, the apparatus comprising a detection layer can also include at least one additional layer. In some embodiments, the apparatus can include at least one of a cover layer, a support layer, and a removable layer. In some embodiments, the apparatus can include any combination of layers described herein.

In some embodiments, the detection layer comprises a lateral flow assay. In some embodiments, the lateral flow assay can rely on antibody-analyte interactions to determine the presence of drugs in an alcoholic or non-alcoholic beverage. In some embodiments, the lateral flow assay can include an anti-analyte antibody that is conjugated to colored particles which can be carried through a chromatographic membrane upon which a analyte-conjugated protein (test line) and an anti-species antibody (control line) are immobilized.

In some embodiments, the lateral flow assay can have an extended storage life. In some embodiments, the detection layer comprising a lateral flow assay (and apparatus) can be laminated to provide protection from external environment without compromising the integrity of the test by permitting gas permeability during use.

In some embodiments, a first indicator signals a portion of at least one of a word, symbol, or character and a second indicator signals a portion of at least one of a word, symbol, or character. In some embodiments, the signal of the first indicator only signals to a user the presence of the targeted substance and wherein the signal of both the first indicator and the second indicator signals to a user the absence of a targeted substance.

Non-limiting embodiments include:
1. An apparatus for detecting the presence of an analyte in a liquid, the apparatus comprising a lateral flow assay capable of receiving a sample of a beverage and analyzing the beverage for the presence of the analyte.
2. The embodiment of paragraph 1, wherein the apparatus comprises: a sample area, a conjugate area, and a detection area, wherein at least one of the sample area, conjugate area, or detection area comprises at least one residual buffer composition.
3. The embodiment of paragraph 2, wherein the conjugate area comprises at least one anti-analyte antibody-particle conjugate or anti-analyte aptamer-particle conjugate;

wherein the detection area comprises a chromatographic membrane and at least one analyte-conjugate protein, and wherein the sample area is configured for receiving a liquid.

4. The embodiment of paragraph 2 or 3, wherein the detection area further comprises at least one anti-species antibody or anti-species aptimer.

5. The embodiment of any one of paragraphs 2-4, wherein the sample area, conjugate area, and the detection area are located on a single pad.

6. The embodiment of any one of paragraphs 2-4, wherein at least one of the sample area, conjugate area, and the detection area is located on a separate pad.

7. The embodiment of any one of paragraphs 3-6, wherein the chromatographic membrane comprises one or more of cellulose, nitrocellulose, polyester fiber, and/or glass fiber.

8. The embodiment of any one of paragraphs 1-7, further comprising a cover defining a pattern, wherein the cover is disposed over the detection area.

9. The embodiment of any one of paragraphs 2-8, wherein the detection area is positioned on or within or under a natural fingernail, an artificial fingernail, a layer of fingernail polish, a fingernail sticker, a fingernail decal, a sticker, a cup, a drink coaster, a drink stirrer, a toothpick, a drink ornament, a pencil, or a pen.

10. The embodiment of any one of paragraphs 2-9, wherein the residual buffer composition comprises at least one surfactant.

11. The embodiment of paragraph 10, wherein the surfactant comprises Pluronic F-68, a fatty alcohol, a polyethylene glycol alkyl ether, a polypropylene glycol alkyl ether, a glucoside alkyl ether, polyethylene glycol octyl, a glycerol alkyl ester, a phenyl ether, polyoxyethylene (20) oleyl ether, octylphenol ethoxylate, a polyethylene glycol alkylphenyl ether, polyethoxylated tallow amine, N,N-bis[3-(D-gluconamido)propyl]cholamide, polyoxyethylene (20) cetyl ether, dimethyldecylphosphine oxide, branched octylphenoxy poly(ethyleneoxy)ethanol, a polyoxyethylene-polyoxypropylene block copolymer, t-octylphenoxypolyethoxyethanol, polyoxyethylene (20) sorbitan monooleate, or a combination thereof.

12. The embodiment of any one of paragraphs 2-11, wherein the residual buffer composition comprises at least one buffer salt.

13. The embodiment of paragraph 12 wherein the buffer salt comprises monosodium phosphate, disodium phosphate, sodium tetraborate, Tris(hydroxymethyl)methylaminopropanesulfonic (TAPS), N-cyclohexyl-2-aminoethanesulfonic acid (CHES), N-tris(hydroxymethyl)methyl-4-aminobutanesulfonic acid (TABS), bis-tris methane (Bis TRIS), tris(hydroxymethyl)aminomethane (TRIS), 2-[[1,3-dihydroxy-2-(hydroxymethyl)propan-2-yl]amino]ethanesulfonic acid (TES), 2-(N-morpholino)ethanesulfonic acid (MES), N-(carbamoylmethyl)iminodiacetic acid (ADA), N-(2-acetamido)-2-aminoethanesulfonic acid (ACES), bis tris propane, piperazine-N,N'-bis(2-ethanesulfonic acid)(PIPES), N-(2-acetamido)-2-aminoethanesulfonic acid (ACES), 3-morpholino-2-hydroxypropanesulfonic acid (MOPSO), cholamine chloride, (3-(N-morpholino)propanesulfonic acid) (MOPS), N,N-bis(2-hydroxyethyl)taurine (BES), N,N-bis(2-hydroxyethyl)-3-amino-2-hydroxypropanesulfonic acid (DIPSO), 4-(N-morpholino)butanesulfonic acid (MOBS), 3-[N-rris(hydroxymethyl)methylamino]-2-hydroxypropanesulfonic acid (TAPSO), acetamidoglycine, triethanolamine(TEA), piperazine-N,N'-bis(2-hydroxypropanesulfonic acid) POPSO, 4-(2-hydroxyethyl)piperazine-1-(2-hydroxypropanesulfonic acid) hydrate (HEPPSO), 3-[4-(2-hydroxyethyl)-1-piperazinyl]propanesulfonic acid (HEPPS), tricine, tris(hydroxymethyl)aminomethane, trometamol (TRIZMA), glycinamide, glycyl-glysine, N-(2-hydroxyethyl)piperazine-N'-(4-butanesulfonic acid) (HEPBS), bicine, 2-amino-2-methyl-1-propanol (AMP), N-(1,1-dimethyl-2-hydroxyethyl)-3-amino-2-hydroxypropanesulfonic acid (AMPSO), N-cyclohexyl-2-hydroxyl-3-aminopropanesulfonic acid (CAPSO), N-cyclohexyl-3-aminopropanesulfonic acid (CAPS), 4-(cyclohexylamino)-1-butanesulfonic acid (CABS), and (4-(2-hydroxyethyl)-1-piperazineethanesulfonic acid) (HEPES), carnitine, gamma-aminobutyric acid, taurine, or salts of amino acids alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine.

14. The embodiment of any one of paragraphs 2-13, wherein the sample area comprises a residual sample area buffer composition, and wherein the residual sample area buffer composition comprises a potassium salt of a weak acid and at least one surfactant.

15. The embodiment of any one of paragraphs 2-14, wherein the conjugate area comprises a residual conjugate area buffer composition, and wherein the residual conjugate area buffer composition comprises a Good's buffer salt and one or more of a protein, an oligomer, a polymer, and a surfactant.

16. The embodiment of any one of paragraphs 2-15, wherein the detection area comprises a residual chromatographic membrane buffer composition, and wherein the residual chromatographic membrane buffer composition comprises a phosphate salt and one or more of a saccharide, a protein, an oligomer, and a polymer.

17. The embodiment of any one of paragraphs 2-16, wherein the lateral flow assay is configured to detect multiple analytes.

18. The embodiment of any one of paragraphs 2-17, wherein the residual buffer composition can reduce the acidity of a test liquid.

19. The embodiment of any one of paragraphs 2-18, wherein the residual buffer composition can increase the viscosity of a test liquid.

20. The embodiment of any one of paragraphs 2-19 wherein the residual buffer composition can substantially reduce or substantially remove the appearance of colored components of a test liquid.

21. A method of detecting an analyte in a liquid, said method comprising: providing the apparatus of any one of paragraphs 1-20; exposing a portion of the apparatus to the liquid; and observing a visual indication to determine presence or absence of the analyte.

22. The embodiment of paragraph 21, wherein the liquid is a beverage.

23. The embodiment of paragraph 21, wherein the liquid is a food extract.

24. The embodiment of any one of paragraphs 21-23, wherein the liquid has a pH from about 4.5 to about 6.8.

25. A method of making an apparatus for detecting the presence of an analyte in a liquid, the method comprising: applying a buffer solution to at least one of a conjugate pad comprising a conjugate area comprising at least one anti-analyte antibody-particle conjugate or anti-analyte aptamer-particle conjugate; a detection area comprising a chromatographic membrane and an analyte-conjugate protein; or a sample area for receiving a liquid; drying the buffer solution; and assembling the conjugate pad, detection area, sample area and a wick so that the sample area is in contact with a portion of the conjugate area, another portion of the conjugate area is in contact with a proximal end of the detection area, and the wick is in contact with a distal end of the detection area.

The apparatus and methods of the appended claims are not limited in scope by the specific apparatus and methods described herein, which are intended as illustrations of a few aspects of the claims and any apparatus and methods that are functionally equivalent are intended to fall within the scope of the claims. Various modifications of the apparatus and methods in addition to those shown and described herein are intended to fall within the scope of the appended claims. For example, additional specific embodiments of apparatus, systems, and methods consistent with the present apparatus and methods are described and set forth in a PCT patent application entitled "Apparatus, System, and Method for Detecting a Target Substance," applied for by Undercover Colors, Inc. and filed on the same day as the present application, which is incorporated by reference in its entirety.

Further, while only certain representative apparatus materials and method steps disclosed herein are specifically described, other combinations of the apparatus materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

EXAMPLES

Example 1

Lateral Flow Immunoassay

A lateral flow immunoassay of the invention was prepared as follows. A benzo test line solution was prepared using (Benzodiazepine-BSA, 5:1 ratio) solution diluted to 2 mg/mL with pH 7.4 Phosphate Buffered Saline (1×). A benzo control line solution was prepared using Goat Anti-Mouse Antibody solution diluted to 1 mg/mL with pH 7.4 Phosphate Buffered Saline (1×). A test line of the diluted benzo test line solution was printed 12 mm from the bottom of the FF120HP (GE Healthcare) nitrocellulose strip, which has a capillary rise time of about 120 seconds for 4 cm. A control line of diluted benzo control line solution was printed 1.5 mm above the test line. The printed strip was placed in a forced air oven to dry for 60 minutes at 10% humidity and 37° C., and then it was stored in a desiccator at 20% humidity until used. The printed FF120HP nitrocellulose strip was treated with the Abcam Immunoassay Buffer (BSA Free), and was placed in a forced air oven to dry for 60 minutes at 10% humidity and 37° C., and then it was stored in a desiccator at 20% humidity until used.

Monoclonal Mouse Anti-Benzodiazepine Antibody-Gold NP conjugate was prepared by first desalting the Monoclonal Mouse Anti-Benzodiazepine Antibody solution using a Zeba spin columns (Thermo Scientific, PN: 89882) to replace the stock buffer with 100 mM, pH 7.4 sodium phosphate buffer. The desalted Monoclonal Mouse Anti-Benzodiazepine Antibody solution in PBS was then conjugated to 40 nm colloidal gold nanoparticles in 50 mM Sodium Borate Buffer. During the conjugation process the 5 mM Sodium Borate buffer with 5% BSA is added to the conjugation solution. Upon completion of the conjugation of the Monoclonal Mouse Anti-Benzodiazepine Antibody to the 40 nm gold NP, the Monoclonal Mouse Anti-Benzodiazepine Antibody-Gold NP conjugate was concentrated and subsequently diluted to OD10 with 100 mM Sodium Borate buffer containing 0.5% Fish Skin Gelatin and 0.1% Tween 80.

A conjugate pad was prepared by pretreating a strip of Ahlstrom 8964 glass fiber pad with 50 mM Sodium Borate containing 1% BSA, 5% Sucrose, 2% Trehalose, 0.25% Tween 20, and 0.15M KCl, and then the pretreated 6614 strip was placed in a forced air oven for 60 minutes at 10% humidity and 37° C., and then stored in a desiccator at 20% humidity until used. The buffered diluted conjugate solution was printed continuously across the 8864 strip at a rate of 8 uL per centimeter, and then the strip was placed in a forced air oven for 60 minutes at 10% humidity and 40° C., and then stored in a desiccator at 20% humidity.

To prepare the sample pad a strip of CF4 (GE Healthcare) was treated with 1M $K_2CO_3$, and then the strip was placed in a forced air oven for 60 minutes at 10% humidity and 40° C., and then stored in a desiccator at 20% humidity. The master card was assembled by applying a printed strip of nitrocellulose to an adhesive backing. The conjugate pad was applied so as to achieve an overlap of 2 mm with the bottom of the nitrocellulose. The sample pad was applied so as to achieve an overlap of 2 mm with the bottom of the conjugate pad. An Ahlstrom 319 wicking pad was applied as to achieve an overlap of 2 mm with the top of the nitrocellulose. The master card was then cut into 4 mm wide strips.

Example 2

Preparation of Buffer Solutions

Buffer solutions were prepared as follows:
Antibody Desalting Buffer Solution: A 100 mM sodium phosphate, pH 7.5 buffer was prepared by combining, in order:
Molecular Biology Reagent Water (Sigma, PN: W4502) was added in the amount of: 80% of total batch volume
Sodium phosphate monobasic (Sigma, PN: S3139) was added in the amount of: 10.2 g/L×batch volume (L)
Sodium phosphate dibasic (Sigma, PN: S9763 was added in the amount of: 58.91 g/L×batch volume (L)
Molecular Biology Reagent Water (Sigma, PN: W4502) to final volume
pH was adjusted to 7.5 using NaOH or concentrated HCl.
Conjugation Blocking Buffer Solution: A 50 mM sodium borate, 10% BSA, pH 9.0 buffer was prepared by combining, in order:
Sodium tetraborate decahydrate (Fisher, PN: AC41945-0010): 11.4 g/L Boric acid (Fisher, PN: A74-1): 1 g/L
Bovine serum albumin (BSA, Equitech, PN: BAH64): 100 g/L
Molecular Biology Reagent Water (Sigma, PN: W4502) to final volume
pH was adjusted to 9.0 using NaOH or HCl, and then the buffer was filtered using a 0.2 μm filter (VWR, PN: 73520-994).

Conjugate Dilution Buffer Solution: A 50 mM sodium borate, 1% BSA, 5% trehalose, and 20% sucrose, pH 9.0 buffer was prepared by combining, in order:
- a. Sodium tetraborate decahydrate (Fisher, PN: AC41945-0010): 11.4 g/L
- b. Boric acid (Fisher, PN: A74-1): 1 g/L
- c. Bovine serum albumin (BSA, Equitech, PN: BAH64): 10 g/L
- d. Sucrose (Sigma, PN: 84097)
- e. Trehalose (Sigma, PN: 90210)
- f. Molecular Biology Reagent Water (Sigma, PN: W4502) to final volume Chromatographic Membrane Buffer Solution: A 10 mM sodium phosphate, 0.1% sucrose, 0.1% BSA, 0.2% PVP-40, pH 7.5 buffer was prepared by combining, in order, per liter of buffer:
Sodium phosphate monobasic (Sigma, PN: S3139), 0.204 g
Sodium phosphate dibasic (Sigma, PN: S9763), 1.178 g
Sucrose (Sigma, PN: 84097) 1.0 g
Bovine serum albumin (BSA, Equitech, PN: BA H64). 1.0 g
Poly(vinylpyrrolidone)-40 (PVP-40, Sigma, PN: PVP-40): 2.0 g
Molecular Biology Reagent Water (Sigma, PN: W4502) to one liter.
pH was adjusted to 7.2 using NaOH or HCl, and then the buffer was filtered using a 0.2 μm filter (VWR, PN: 73520-994).

Conjugate Pad Buffer Solution: A 0.5 M Tris, 3% BSA, 1% PVP-40, 0.25% Triton X-100, 0.5% Pluronic F-68, pH 8.0 buffer was pre prepared by combining, in order:
Tris base (Sigma, PN: T1375): 114.8 g/L
Bovine serum albumin (BSA, Equitech, PN: BAH64): 30 g/L
Polyvinylpyrrolidone-40 (PVP-40, Sigma, PN: PVP-40): 10 g/L
Triton X-100 (Sigma, PN: T8787): 2.5 g/L
Pluronic F-68 (Thermo Fisher, PN: 24040032): 5 g/L
Add Molecular Biology Reagent Water (Sigma, PN: W4502) to final volume Sample Area Buffer Solution: A 1.0 M Potassium Carbonate ($K_2CO_3$) buffer with 0.25% Triton X-305, pH 7.0 buffer was pre prepared by combining, in order:
Potassium carbonate (Sigma PN: P1472): 138.2 g/L
Triton X-305 (Sigma, PN: X305): 3.6 g/L
Add Molecular Biology Reagent Water (Sigma, PN: W4502) to final volume Example 3

Preparation of a Lateral Flow Assay with a Combined Sample-Conjugate Pad

A lateral flow immunoassay of the invention was prepared as follows. A benzo test line solution was prepared using (Benzodiazepine-BSA, 5:1 ratio) solution diluted to 4 mg/mL with pH 7.4 Phosphate Buffered Saline (1×). A benzo control line solution was prepared using Goat Anti-Mouse Antibody solution diluted to 1 mg/mL with pH 7.4 Phosphate Buffered Saline (1×). A test line of the diluted benzo test line solution was printed 5 mm from the bottom of the 8 mm wide CN095 (Sartorius) nitrocellulose strip, which has a capillary rise time of about 85±10 seconds for 4 cm. A control line of diluted benzo control line solution was printed 2 mm above the test line. The printed strip was placed in a forced air oven to dry for 30 minutes at 10% humidity and 40° C., and then it was stored for 16 hours in a desiccator at 20% humidity. The printed CN095 nitrocellulose strip (Sartorius) was treated with the Chromatographic Membrane Buffer described above in Example 2, and was placed in a forced air oven to dry for 30 minutes at 10% humidity and 40° C., and then it was stored for 16 hours in a desiccator at 20% humidity.

Monoclonal Mouse Anti-Benzodiazepine Antibody-Gold NP conjugate was prepared by first desalting the Monoclonal Mouse Anti-Benzodiazepine Antibody solution using a Zeba spin columns (Thermo Scientific, PN: 89882) to replace the stock buffer with 100 mM, pH 7.4 sodium phosphate buffer. The desalted Monoclonal Mouse Anti-Benzodiazepine Antibody solution in PBS was then conjugated to 40 nm colloidal gold nanoparticles. During the conjugation process the Conjugation Blocking Buffer is added to the conjugation solution. Upon completion of the conjugation of the Monoclonal Mouse Anti-Benzodiazepine Antibody to the 40 nm gold NP, the Monoclonal Mouse Anti-Benzodiazepine Antibody-Gold NP conjugate was concentrated and subsequently diluted to OD15 with the Conjugate Dilution Buffer as described above in Example 2.

A combined sample-conjugate pad was prepared by pretreating a strip of Ahlstrom 6614 polyester fiber pad with Conjugate Pad Buffer described above in Example 2, and then the pretreated 6614 strip was placed in a forced air oven for 60 minutes at 10% humidity and 40° C., and then stored for 16 hours in a desiccator at 20% humidity. To prepare the sample area of the combined sample-conjugate pad, only the sample area of an Ahlstrom 6614 polyester fiber pad was treated with the Sample Area Buffer described above in Example 2. The buffered diluted conjugate solution was printed continuously across the strip on 6614 in only the conjugate area at a rate of 5 per centimeter, and then the strip was placed in a forced air oven for 60 minutes at 10% humidity and 40° C., and then stored for 16 hours in a desiccator at 20% humidity.

The master card was assembled by applying a printed strip of nitrocellulose to an adhesive backing. The sample/conjugate pad was applied so as to achieve an overlap of 2 mm with the bottom of the nitrocellulose. An Ahlstrom 319 wicking pad was applied as to achieve an overlap of 2 mm with the top of the nitrocellulose. The master card was then cut into 4 mm wide strips.

Example 4

The Effect of $K_2CO_3$ and TRIS Sample Pad Treatment on Lateral Flow Assay Results Lateral flow assays were prepared by the process of Example 3, except that the assays of Table 1 had no sample pad/area pretreatment, and the assays of Table 2 were pretreated with a sample area buffer solution comprising potassium carbonate. A check indicates no assay failure. An X equals false negative results due to non-specific binding of conjugate to test line. The false negative results were overcome by pre-treatment, with one exception of hot coffee.

Procedure:
1.) Prepare assays according to the procedure described in Example 3. Prepare half of the assays without the addition of the Sample Area Buffer.
2.) Prepare individual spiked solutions of each beverage listed. The beverages are spiked with either Alprazolam, Diazepam, or Flunitrazepam to a final concentration of 1000 ng/mL.

3.) Deposit 20 μL of the designated blank beverage on the untreated sample area of three assays per designated beverage and record the results at 1 minute.

4.) Deposit 20 μL of the designated spiked beverage on the untreated sample area of three assays per designated beverage and record the results at 1 minute.

5.) Deposit 20 μL of the designated blank beverage on the treated sample area of three assays per designated beverage and record the results at 1 minute.

6.) Deposit 20 μL of the designated spiked beverage on the treated sample area of three assays per designated beverage and record the results at 1 minute.

TABLE 1

No potassium carbonate pre-treatment of sample pad/area.

| | | Valium (diazepam) | Xanax (alprazolam) | Rohypnol (flunitrazepam) |
|---|---|---|---|---|
| Beer/Other | Sam Adams Boston Lager | ✓ | ✓ | ✓ |
| | Guinness | ✓ | ✓ | ✓ |
| | Blue Moon | ✓ | ✓ | ✓ |
| | Big Boss Bad Penny | ✓ | ✓ | ✓ |
| | Lonerider Shotgun Betty Hefeweizen | ✓ | ✓ | ✓ |
| | Foothills People's Porter | ✓ | ✓ | ✓ |
| | Duck-Rabbit Amber | ✓ | ✓ | ✓ |
| | Sweetwater IPA | ✓ | ✓ | ✓ |
| | Sierra Nevada Pale Ale | ✓ | ✓ | ✓ |
| | Bell's Oberon | ✓ | ✓ | ✓ |
| | Mike's Hard Lemonade | X | X | X |
| | Angry Orchard Cider | X | X | X |
| White Wine | Yellowtail Pinot Grigio | X | ✓ | ✓ |
| | Barefoot Moscato | X | X | X |
| | Gallo Chardonnay | ✓ | ✓ | ✓ |
| | Mondavi Woodbridge Sauvignon Blanc | X | X | X |
| | Barefoot Riesling | X | X | ✓ |
| Rose Wine | Gallo White Merlot | X | X | X |
| | Sutter Home Pink Moscato | X | ✓ | X |
| | Yellowtail Pink Moscato | X | X | X |
| | Barefoot Red Moscato | ✓ | ✓ | ✓ |
| | Mondavi Woodbridge White Zinfandel | X | X | X |
| Red Wine | Yellowtail Merlot | X | X | X |
| | Sutter Home Pinot Noir | X | X | X |
| | Barefoot Shiraz | ✓ | ✓ | ✓ |
| | Mondavi Woodbridge Zinfandel | ✓ | ✓ | ✓ |
| | Gallo Cabernet Sauvignon | ✓ | ✓ | ✓ |
| Mixed Drinks | Rum and Coke | ✓ | ✓ | ✓ |
| | Martini | ✓ | ✓ | ✓ |
| | Mojito | X | X | X |
| | Old Fashioned | ✓ | ✓ | ✓ |
| | Long Island Iced Tea | X | X | X |
| | White Russian | ✓ | ✓ | ✓ |
| | Pina Colada | ✓ | ✓ | ✓ |
| | Jose Cuervo Ready to Drink Classic Margarita | ✓ | ✓ | ✓ |
| | Screwdriver | ✓ | ✓ | ✓ |
| | Cosmopolitan | ✓ | ✓ | ✓ |
| | Tequila Sunrise | ✓ | ✓ | ✓ |
| | Margarita | X | X | X |
| | Daiquiri | X | X | X |
| | Irish Coffee | X | X | X |
| | Bloody Mary | ✓ | ✓ | ✓ |
| Liquor | Smirnoff Vodka | ✓ | ✓ | ✓ |
| | Captain Morgan Spiced Rum | ✓ | ✓ | ✓ |
| | Jack Daniel's Whiskey | ✓ | ✓ | ✓ |
| | Jagermeister | ✓ | ✓ | ✓ |
| | Tanqueray Gin | X | X | X |
| | Bacardi Rum | ✓ | ✓ | ✓ |
| | Crown Royal Whisky | X | X | X |
| | Jim Beam Bourbon | ✓ | ✓ | ✓ |
| | Jose Cuervo Tequila | ✓ | ✓ | ✓ |
| | Fireball Cinnamon Whisky | ✓ | ✓ | ✓ |
| | Dekuyper Peachtree | ✓ | ✓ | ✓ |
| | Malibu Coconut Rum | ✓ | ✓ | ✓ |
| Mixers | Cranberry Juice | ✓ | ✓ | ✓ |
| | Lemonade | ✓ | X | X |
| | Hawaiian Punch | ✓ | ✓ | ✓ |
| | Half and Half | ✓ | ✓ | ✓ |
| | Coffee (hot) | X | X | X |
| | Orange Juice | ✓ | ✓ | ✓ |
| | Rose's Mojito Mix | X | X | X |
| | Tonic Water | ✓ | ✓ | ✓ |
| | Pineapple Juice | X | X | X |
| | Coke | ✓ | ✓ | ✓ |
| | V8 | ✓ | ✓ | ✓ |
| | Club Soda | ✓ | ✓ | ✓ |
| | Lime Juice | X | X | X |

TABLE 2

With potassium carbonate pre-treatment of sample pad/area.

| | | Valium (diazepam) | Xanax (alprazolam) | Rohypnol (flunitrazepam) |
|---|---|---|---|---|
| Beer/Other | Sam Adams Boston Lager | ✓ | ✓ | ✓ |
| | Guinness | ✓ | ✓ | ✓ |
| | Blue Moon | ✓ | ✓ | ✓ |
| | Big Boss Bad Penny | ✓ | ✓ | ✓ |
| | Lonerider Shotgun Betty Hefeweizen | ✓ | ✓ | ✓ |
| | Foothills People's Porter | ✓ | ✓ | ✓ |
| | Duck-Rabbit Amber | ✓ | ✓ | ✓ |
| | Sweetwater IPA | ✓ | ✓ | ✓ |
| | Sierra Nevada Pale Ale | ✓ | ✓ | ✓ |
| | Bell's Oberon | ✓ | ✓ | ✓ |
| | Mike's Hard Lemonade | ✓ | ✓ | ✓ |
| | Angry Orchard Cider | ✓ | ✓ | ✓ |
| White Wine | Yellowtail Pinot Grigio | ✓ | ✓ | ✓ |
| | Barefoot Moscato | ✓ | ✓ | ✓ |
| | Gallo Chardonnay | ✓ | ✓ | ✓ |
| | Mondavi Woodbridge Sauvignon Blanc | ✓ | ✓ | ✓ |
| | Barefoot Riesling | ✓ | ✓ | ✓ |
| Rose Wine | Gallo White Merlot | ✓ | ✓ | ✓ |
| | Sutter Home Pink Moscato | ✓ | ✓ | ✓ |
| | Yellowtail Pink Moscato | ✓ | ✓ | ✓ |
| | Barefoot Red Moscato | ✓ | ✓ | ✓ |
| | Mondavi Woodbridge White Zinfandel | ✓ | ✓ | ✓ |
| Red Wine | Yellowtail Merlot | ✓ | ✓ | ✓ |
| | Sutter Home Pinot Noir | ✓ | ✓ | ✓ |
| | Barefoot Shiraz | ✓ | ✓ | ✓ |
| | Mondavi Woodbridge Zinfandel | ✓ | ✓ | ✓ |
| | Gallo Cabernet Sauvignon | ✓ | ✓ | ✓ |
| Mixed Drinks | Rum and Coke | ✓ | ✓ | ✓ |
| | Martini | ✓ | ✓ | ✓ |
| | Mojito | ✓ | ✓ | ✓ |
| | Old Fashioned | ✓ | ✓ | ✓ |
| | Long Island Iced Tea | ✓ | ✓ | ✓ |
| | White Russian | ✓ | ✓ | ✓ |
| | Pina Colada | ✓ | ✓ | ✓ |
| | Jose Cuervo Ready to Drink Classic Margarita | ✓ | ✓ | ✓ |
| | Screwdriver | ✓ | ✓ | ✓ |
| | Cosmopolitan | ✓ | ✓ | ✓ |
| | Tequila Sunrise | ✓ | ✓ | ✓ |
| | Margarita | ✓ | ✓ | ✓ |
| | Daiquiri | ✓ | ✓ | ✓ |
| | Irish Coffee | ✓ | ✓ | ✓ |
| | Bloody Mary | ✓ | ✓ | ✓ |

TABLE 2-continued

With potassium carbonate pre-treatment of sample pad/area.

|  |  | Valium (diazepam) | Xanax (alprazolam) | Rohypnol (flunitrazepam) |
|---|---|---|---|---|
| Liquor | Smirnoff Vodka | ✓ | ✓ | ✓ |
|  | Captain Morgan Spiced Rum | ✓ | ✓ | ✓ |
|  | Jack Daniel's Whiskey | ✓ | ✓ | ✓ |
|  | Jagermeister | ✓ | ✓ | ✓ |
|  | Tanqueray Gin | ✓ | ✓ | ✓ |
|  | Bacardi Rum | ✓ | ✓ | ✓ |
|  | Crown Royal Whisky | ✓ | ✓ | ✓ |
|  | Jim Beam Bourbon | ✓ | ✓ | ✓ |
|  | Jose Cuervo Tequila | ✓ | ✓ | ✓ |
|  | Fireball Cinnamon Whisky | ✓ | ✓ | ✓ |
|  | Dekuyper Peachtree | ✓ | ✓ | ✓ |
|  | Malibu Coconut Rum | ✓ | ✓ | ✓ |
| Mixers | Cranberry Juice | ✓ | ✓ | ✓ |
|  | Lemonade | ✓ | ✓ | ✓ |
|  | Hawaiian Punch | ✓ | ✓ | ✓ |
|  | Half and Half | ✓ | ✓ | ✓ |
|  | Coffee (hot) | X | X | X |
|  | Orange Juice | ✓ | ✓ | ✓ |
|  | Rose's Mojito Mix | ✓ | ✓ | ✓ |
|  | Tonic Water | ✓ | ✓ | ✓ |
|  | Pineapple Juice | ✓ | ✓ | ✓ |
|  | Coke | ✓ | ✓ | ✓ |
|  | V8 | ✓ | ✓ | ✓ |
|  | Club Soda | ✓ | ✓ | ✓ |
|  | Lime Juice | ✓ | ✓ | ✓ |

Example 5

Faster Development of Test Results in Inventive Assays vs. Comparative Assays

Lateral flow assays were prepared by the process of Example 3 and were compared to commercial lateral flow assays (DBZ-114 distributed by Innovacon, San Diego, Calif.) 30 seconds after exposure to a test fluid. The inventive assay results are fully developed by 30 seconds, whereas the comparative assays had not fully developed at 30 seconds.

Figure 3:
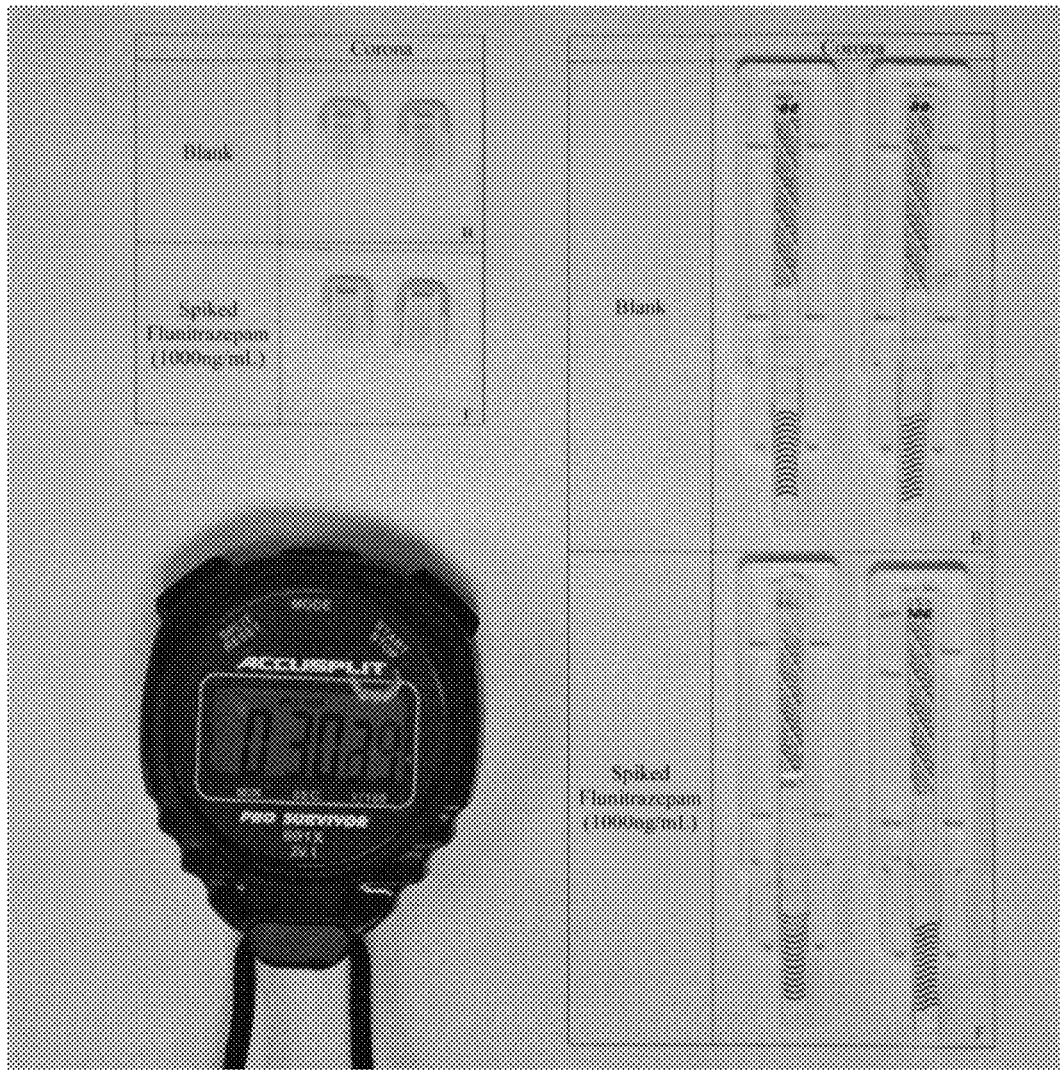
FIG. 3 shows test results of comparative assays and inventive assays according to some embodiments described herein.

Procedure:
1.) Prepare assays according to the procedure described in Example 3. To prepare linear assays use a rectangular Ahlstrom 319 wick. To prepare miniaturized assays use the U-shaped Ahlstrom 319 wick.
2.) Arrange the miniaturized and linear assays on the testing sheet.
3.) Deposit 20 μL of blank Corona beer on the sample area of the linear assays marked blank.
4.) Deposit 20 μL of Corona beer spiked with 1000 ng/mL Flunitrazepam on the sample area of the linear assays.
5.) Deposit 20 μL of blank Corona beer on the sample pad of the U-wick assays marked blank.
6.) Deposit 20 μL of Corona beer spiked with 1000 ng/mL Flunitrazepam on the sample pad of the U-wick assays.
7.) Take picture at 30 seconds Results are shown in FIG. 3 with the lateral flow assays prepared by Example 3 shown on the left and the commercial lateral flow assays shown on the right.

Example 6

Beverage Components Cause False Negative Results in Comparative Assays, but not in Inventive Assays Comparative commercial assays as used in Example 5 fail (due to false negatives) in whiskey and moscato after 5 minutes of development due to specifications of the commercial assay. The commercial assay completely fails to run in daiquiri, and no results are visible after 5 minutes. The inventive assays (prepared as in Example 3) perform successfully in all cases, with no false negative results.

Procedure:
1.) Prepare miniature assays according to the procedure described in Example 3.
2.) Arrange the miniaturized and commercial assays on the testing sheet.
3.) Deposit 20 μL of the designated blank beverage on the sample area of the miniature assays marked blank.
4.) Deposit 20 μL of designated beverage spiked with 1000 ng/mL Flunitrazepam on the sample area of the miniature assays.
5.) Deposit 100 μL of designated blank beverage on the sample pad of the commercial assays marked blank.
6.) Deposit 100 μL of designated beverage with 1000 ng/mL Flunitrazepam on the sample pad of the commercial assays.
7.) Take picture at 5 minutes to allow time for the commercial assays to fully develop.

Figure 4:
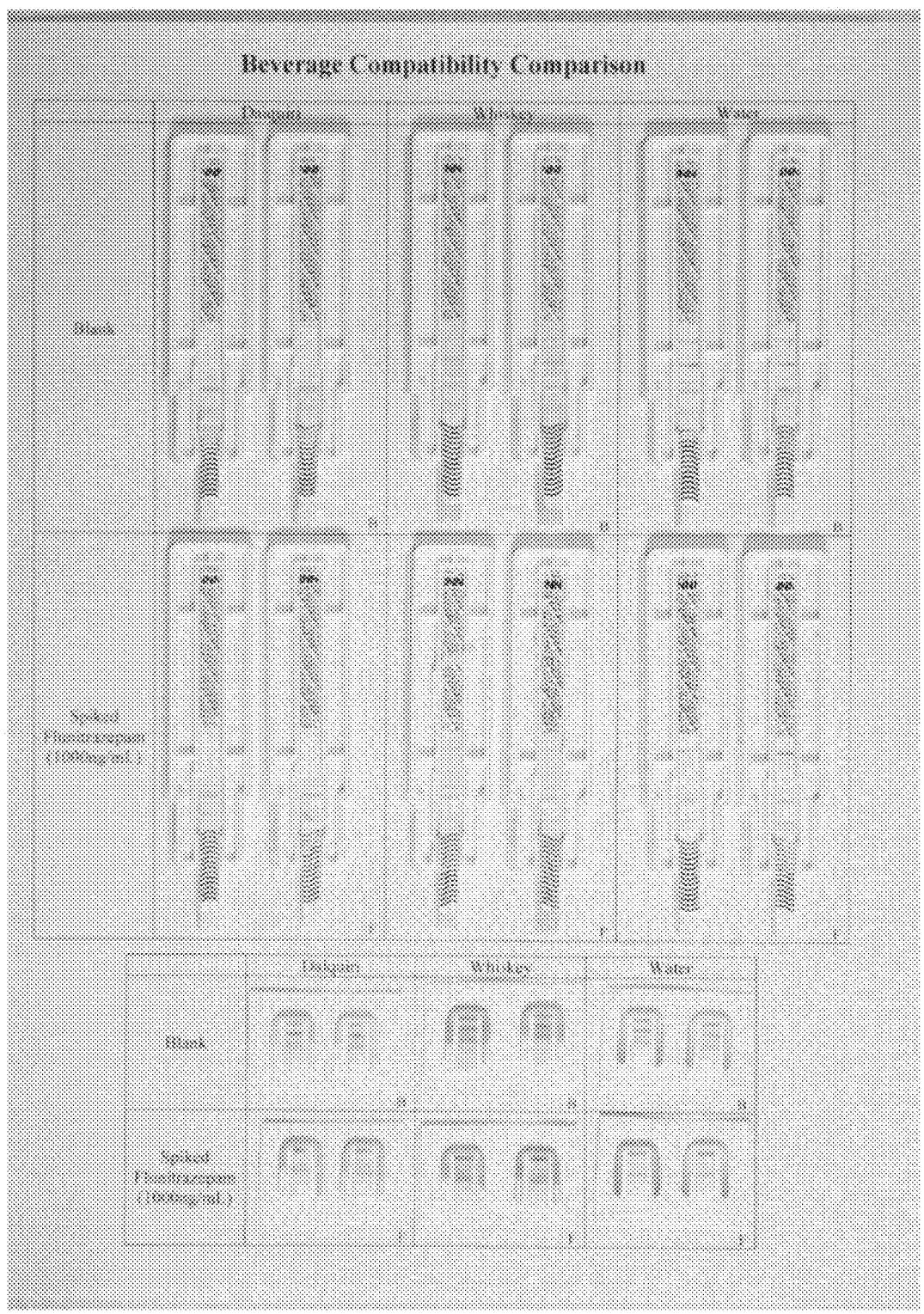
FIG. 4 shows test results of comparative assays and inventive assays according to some embodiments described herein.
Figure 5:
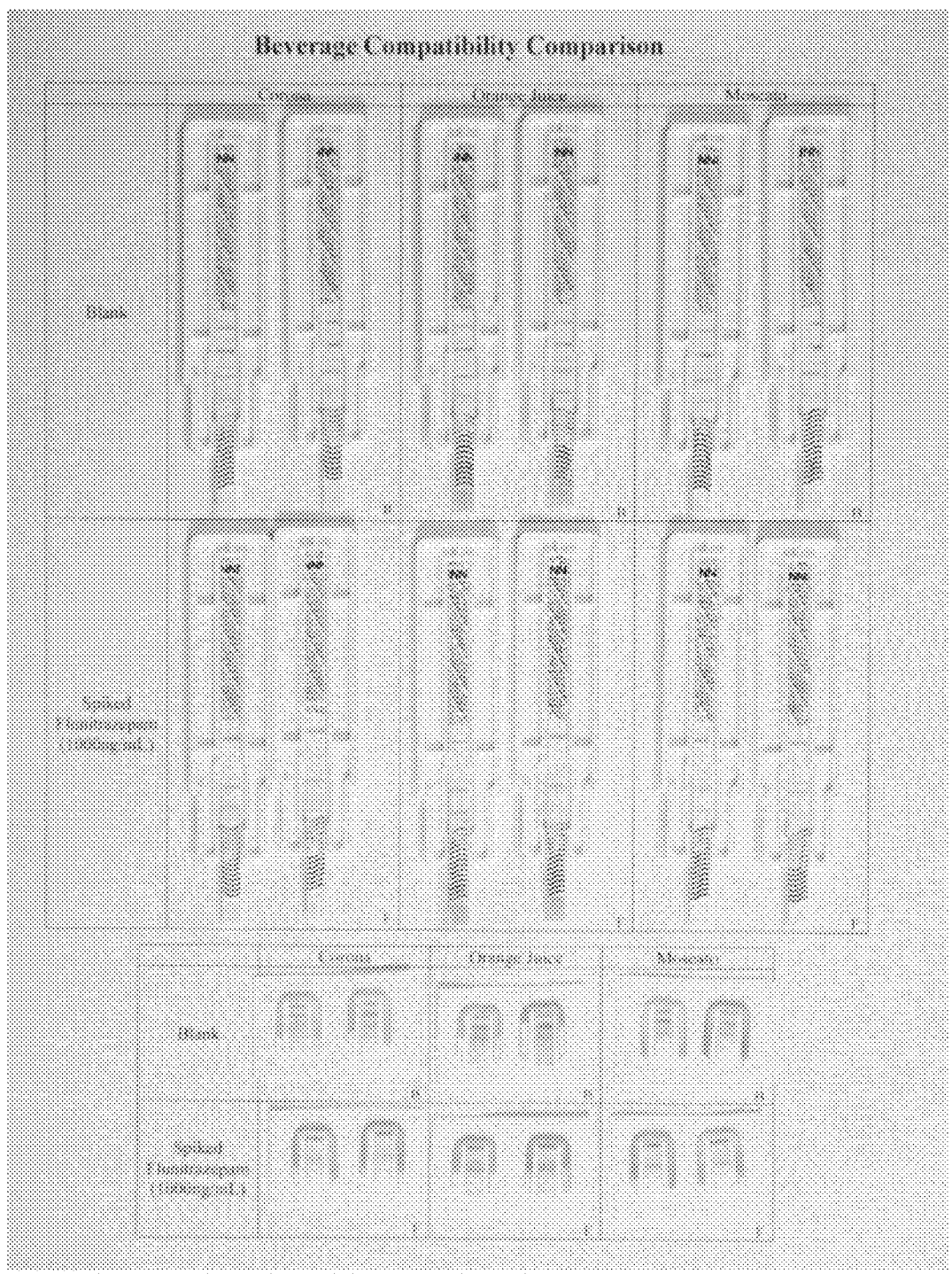
FIG. 5 shows test results of comparative assays and inventive assays according to some embodiments described herein.

Results are shown in FIG. 4 for daiquiri, whisky, and water, and in FIG. 5 for Corona, orange juice, and moscato, with the six commercial assays on top and the six inventive assays on the bottom in both Figures.

Example 7

U-shaped Wick Shortens Assay Length without Affecting Performance

Inventive assays (prepared as in Example 3) with a U-shaped wick (shown on right), where the fluid path is longer than the assay length, perform just as well as inventive assays (prepared as in Example 3) with a linear wick (shown on left), where the fluid path equals the assay length.

Figure 6:
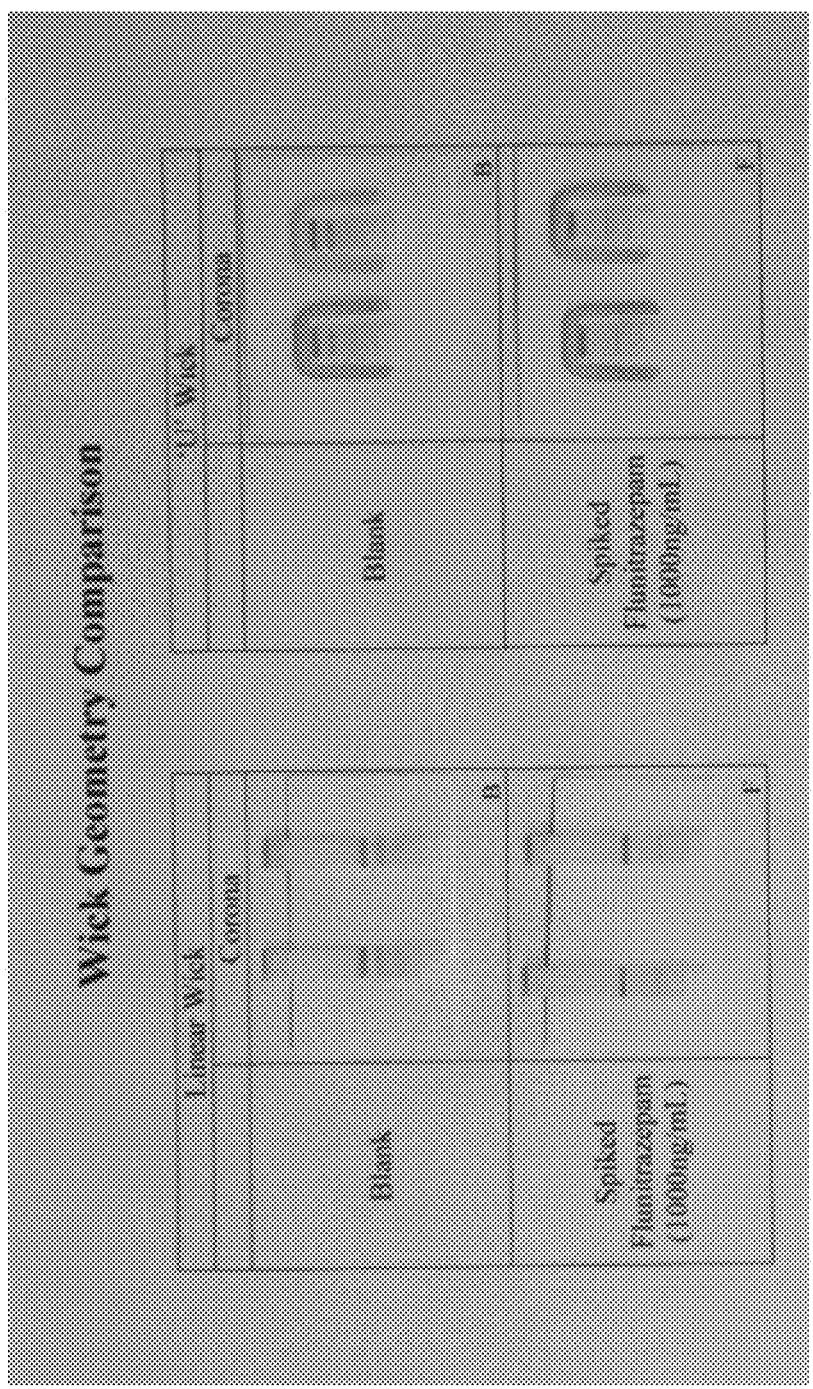
FIG. 6 shows test results of comparative assays and inventive assays according to some embodiments described herein.

Procedure:
1.) Prepare assays according to the procedure described in Example 3. To prepare linear assays use a rectangular Ahlstrom 319 wick. To prepare miniaturized assays use the U-shaped Ahlstrom 319 wick.
2.) Arrange the miniaturized and linear assays on the testing sheet.
3.) Deposit 20 μL of blank Corona on the sample area of the linear assays marked blank.
4.) Deposit 20 μL of Corona spiked with 1000 ng/mL Flunitrazepam on the sample area of the linear assays.
5.) Deposit 20 μL of blank Corona on the sample pad of the U-wick assays marked blank.
6.) Deposit 20 μL of Corona spiked with 1000 ng/mL Flunitrazepam on the sample pad of the U-wick assays.
7.) Take picture at 30 seconds Results are shown in FIG. 6 with the U-shaped wick assays on the right and the linear wick assays on the left.

What is claimed is:

1. An apparatus capable of detecting the presence of an analyte in a beverage, the apparatus comprising a lateral flow assay comprising a sample area for receiving a beverage, a conjugate area adjacent to the sample area but not overlapping the sample area, and a detection area adjacent to the conjugate area, wherein the detection area is in fluid communication with the sample area through the conjugate area,
    wherein the sample area and the conjugate area comprise different areas of a first pad having a length and a width;

wherein the sample area extends along a first portion of the length of the first pad and across the width of the first pad and comprises at least one first buffering compound disposed across the entire sample area, wherein the conjugate area extends along a second portion of the length of the first pad and across the width of the first pad and comprises a marker disposed in the conjugate area and at least one second buffering compound disposed across the entire conjugate area, wherein the composition of the at least one first buffering compound is different from the composition of the at least one second buffering compound;

wherein the detection area comprises an analyte-conjugated protein disposed in the detection area at one or more test lines; and wherein the at least one first buffering compound and the at least one second buffering compound are selected so the apparatus is capable of detecting the presence of the analyte in any one of at least two different beverages.

2. The apparatus of claim 1, wherein the at least two different beverages comprise two or more of a juice, a soda, a wine, a beer, a liquor, or a mixed drink.

3. The apparatus of claim 1, wherein the sample area further comprises a surfactant that can precipitate one or more colored components of a beverage.

4. The apparatus of claim 1, wherein at least one of the at least two different beverages is a mixed drink; wherein the mixed drink comprises a liquor and a mixer; wherein the liquor comprises one or more of vodka, rum, whiskey, gin, bourbon, and tequila; and wherein the mixer comprises one or more of cranberry juice, lemonade, red punch, dairy, orange juice, tonic water, pineapple juice, cola, vegetable juice, club soda, and lime juice.

5. The apparatus of claim 1, wherein the analyte-conjugated protein comprises an analyte that comprises a benzodiazepine, ketamine, 4-hydroxybutanoic acid (GHB), ephedrine, methamphetamine, amphetamine, flunitrazepam, 3,4-methylenedioxy-methamphetamine (MDMA), clonazepam, tetrahydrocannabinol (THC), zolpidem, eszopiclone, ramelteon, zaleplon, doxepine, triazolam, temazepam, diazepam, or alprazolam.

6. The apparatus of claim 1, wherein the analyte-conjugated protein comprises an analyte that comprises a date rape drug.

7. The apparatus of claim 1, wherein the detection area comprises at least two different analyte-conjugated proteins disposed at one or more test lines to detect the presence of at least two different analytes.

8. The apparatus of claim 1, wherein the sample area further comprises a viscosity modifier.

9. The apparatus of claim 1, wherein the apparatus further comprises a clear laminate layer on the detection area.

10. The apparatus of claim 1, wherein the apparatus comprises at least a portion of an artificial fingernail, a layer of fingernail polish, a fingernail sticker, or a fingernail decal, a nail wrap, a ring, a bracelet, a necklace, a charm, or a lanyard.

11. The apparatus of claim 1, wherein the apparatus has a length of 0.5 mm to 20 mm, a width of 0.5 mm to 10 mm, and a thickness of 0.02 mm to 5 mm.

12. The apparatus of claim 1, wherein the at least one first buffering compound comprises a carboxylate salt or tris(hydroxymethyl)aminomethane, and wherein the sample area further comprises at least one surfactant.

13. The apparatus of claim 1, wherein the detection area comprises at least one third buffering compound disposed across the entire detection area.

14. The apparatus of claim 13, wherein the analyte-conjugated protein comprises an analyte that comprises a benzodiazepine, ketamine, 4-hydroxybutanoic acid (GHB), ephedrine, methamphetamine, amphetamine, flunitrazepam, 3,4-methylenedioxy-methamphetamine (MDMA), clonazepam, tetrahydrocannabinol (THC), zolpidem, eszopiclone, ramelteon, zaleplon, doxepine, triazolam, temazepam, diazepam, or alprazolam.

15. The apparatus of claim 1, wherein the analyte-conjugated protein comprises an analyte that comprises a date rape drug.

* * * * *